US008815524B2

(12) United States Patent
Hirokawa et al.

(10) Patent No.: US 8,815,524 B2
(45) Date of Patent: Aug. 26, 2014

(54) IMMUNITY EVALUATION METHOD, IMMUNITY EVALUATION APPARATUS, IMMUNITY EVALUATION PROGRAM AND DATA RECORDING MEDIUM HAVING THE IMMUNITY EVALUATION PROGRAM STORED THEREIN

(75) Inventors: Katsuiku Hirokawa, Tokyo (JP); Masanori Utsuyama, Tokyo (JP); Masanobu Kitagawa, Tokyo (JP)

(73) Assignee: National University Corporation, Tokyo Medical and Dental University, Tokyo (JP)

( * ) Notice: Subject to any disclaimer, the term of this patent is extended or adjusted under 35 U.S.C. 154(b) by 1395 days.

(21) Appl. No.: 12/304,825

(22) PCT Filed: Jun. 15, 2007

(86) PCT No.: PCT/JP2007/062158
§ 371 (c)(1),
(2), (4) Date: Oct. 30, 2009

(87) PCT Pub. No.: WO2007/145333
PCT Pub. Date: Dec. 21, 2007

(65) Prior Publication Data
US 2010/0062473 A1    Mar. 11, 2010

(30) Foreign Application Priority Data
Jun. 15, 2006    (JP) ................................ 2006-166626

(51) Int. Cl.
*G01N 33/50*     (2006.01)
*G01N 33/569*    (2006.01)

(52) U.S. Cl.
CPC ...... *G01N 33/56966* (2013.01); *G01N 2800/24* (2013.01); *G01N 33/5091* (2013.01)
USPC ..................................................... 435/7.21

(58) Field of Classification Search
None
See application file for complete search history.

(56) References Cited

U.S. PATENT DOCUMENTS

| 5,658,744 A | 8/1997 | Ochoa et al. | |
| 2003/0108968 A1 | 6/2003 | Hu | |
| 2005/0032039 A1* | 2/2005 | Sastry et al. | 435/5 |
| 2006/0252075 A1* | 11/2006 | Zagury et al. | 435/6 |

FOREIGN PATENT DOCUMENTS

| JP | 2003052395 | 2/2003 |
| JP | 2003525452 | 8/2003 |
| JP | 2005143798 | 6/2005 |
| JP | 2005143801 | 6/2005 |

OTHER PUBLICATIONS

Technical Bulletin for "CellTiter 96® AQueous One Solution Cell Proliferation Assay" from Promega (2012), 12 pages.*
Giraldo et al., PLOS Neglected Tropical Diseases, 2013, 7: 1-11.*
Supplementary European Search Report issued to European Application No. 07745412.2, mailed Jun. 10, 2009.
Martin Blazik et al., "Leukocyte phenotype and function predicts infection risk in renal transplant recipients", Nephrology Dialysis Transplantation, vol. 20, No. 10 (Oct. 2005) pp. 2226-2230.
Database Biosis [Online] Biosciences Information Services, Philadelphia, PA, US; 1981, Minami T et al., "Immunological Studies on Stomach Cancer Patients with special emphasis on Evaluation of Parameters and Those Scoring", Database accession No. PREV198273077129.
Geert van Poppel et al., "Effect of β-carotene on immunological indexes in healthy male smokers 1-3", American Journal of Clinical Nutrition, vol. 57, No. 3 (1993) pp. 402-407.
Oren Shibolet et al., "Immunomodulation of Experimental Colitis via Caloric Restriction: Role of Nk1.1 + T Cells", Clinical Immunology, vol. 105, No. 1 (Oct. 2002) pp. 48-56.
Masanori Utsuyama et al., "Differential age-change in the Nos. of CD4 + CD45RA + and CD4 + CD29 + T cell subsets in human peripheral blood", Mechanisms of Ageing and Development, vol. 63, No. 1, (Mar. 15, 1992) pp. 57-68.
Katsuiku Hirokawa et al., "Decline of T cell-related immune functions in cancer patients and an attempt to restore them through infusion of activated autologus T cells", Mechanisms of Ageing and Development, vol. 130, No. 1-2 (Jan. 2009) pp. 86-91.
International Search Report for PCT/JP2007/062158 dated Jul. 31, 2007.
K. Hirokawa, "Senescence, Stress and Immune Function", Proceedings of the Japanese Society of Pathology, vol. 89, No. 2, 2000, pp. 21-40.
H. Umehara et al., "Evaluation of Age-related Immune System Change", Inflammation & Immunology, vol. 10, No. 4, 2002, pp. 409-415.
A. Wakikawa et al., Altered expression of various receptors on T cells in young and old mice after mitogenic stimulation: a flow cytometric analysis:, Mechanisms of Ageing and Development, vol. 94, 1997, pp. 113-122.
M. Utsuyama et al., "Differential Age-Change in the Nos. of CD4+CD45RA+ and CD4+CD29+ T Cell Subsets in Human Peripheral Blood", Mechanisms of Ageing and Development, vol. 63, 1992, pp. 57-68.
K. Hirokawa, "Aging and immunity", Japanese Journal of Geriatrics, vol. 40, No. 6, 2003, pp. 543-552.

* cited by examiner

*Primary Examiner* — Ilia Ouspenski
(74) *Attorney, Agent, or Firm* — Hoffmann & Baron, LLP

(57) ABSTRACT

An immunity evaluation method for evaluating immunity by using immune cell markers for immune cells contained in sampled blood comprises the step of determining an evaluation value for each of two or more selected kinds of immune cell markers based on the individual immune cell markers contained in the sampled blood, the step of adding the evaluation values so obtained for the at least two selected kinds of immune cell markers, and the step of evaluating the immunity from the results of the adding.

2 Claims, 24 Drawing Sheets

FIG. 3

| SCORING | (a) T CELLS /μL | (b) T CELL PROLIFERATION INDEX | (c) CD4/CD8 T CELL COUNT RATIO | (d) NAIVE T CELLS/μL | (e) NAIVE/ MEMORY T CELL COUNT RATIO | (f) B CELLS/μL | (g) NK CELLS/μL | (h) IL-2 CYTOKINE PRODUCTIVITY | (i) IFN CYTOKINE PRODUCTIVITY | (j) IL-4 CYTOKINE PRODUCTIVITY |
|---|---|---|---|---|---|---|---|---|---|---|
| 3 | >1178 | >1.68 | 1.3-2.6 | >335 | >1.00 | >80 | >290 | >22.1 | >25.0 | >17.7 |
| 2 | 717-1177 | 0.70-1.67 | 1.0-1.2, 2.6-3.5 | 140-334 | 0.43-0.99 | 11-79 | 65-289 | 20.0-22.0 | 20.7-24.9 | 14.8-17.6 |
| 1 | <716 | <0.69 | <0.99 >3.5 | <139 | <0.42 | <10 | <64 | <19.9 | <20.6 | <14.7 |

| IMMUNITY | POINT |
|---|---|
| GRADE 5 | 30~29 |
| GRADE 4 | 28~26 |
| GRADE 3 | 22~25 |
| GRADE 2 | 21~17 |
| GRADE 1 | 16~10 |

FIG. 10

| (a) | (b) | (c) | (d) | (e) | (f) | (g) | (h) | (i) | (j) |
|---|---|---|---|---|---|---|---|---|---|
| T CELLS /μL | T CELL PROLIFERATION INDEX | CD4/CD8 T CELL COUNT RATIO | NAIVE T CELLS/μL | NAIVE/ MEMORY T CELL COUNT RATIO | B CELLS/μL | NK CELLS/μL | IL-2 CYTOKINE PRODUCTIVITY | IFN CYTOKINE PRODUCTIVITY | IL-4 CYTOKINE PRODUCTIVITY |
| 3 | 1 | 2 | 3 | 2 | 3 | 2 | 2 | 3 | 2 |

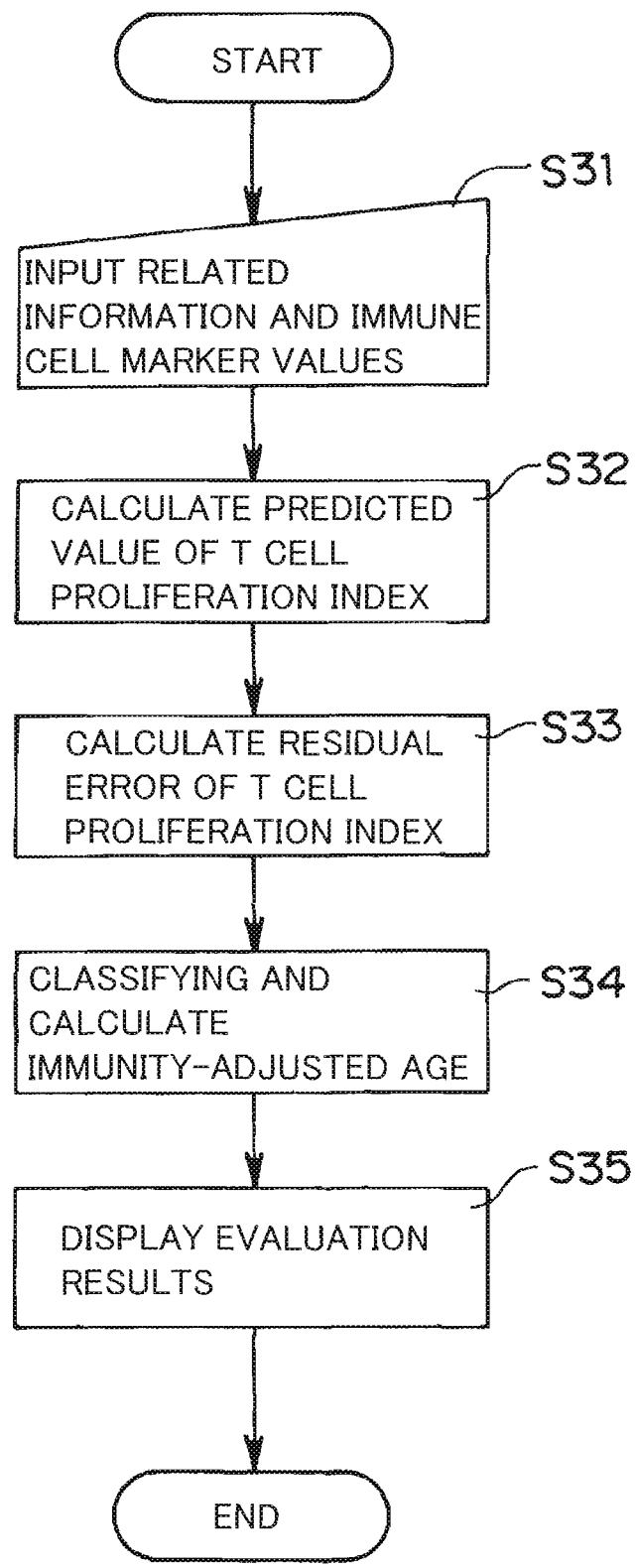

FIG. 16

| | CLASSIFYING MEASURED VALUES | ESTIMATED IMMUNITY-ADJUSTED AGE |
|---|---|---|
| A: | PREDICTED VALUE + 2.0 SD < MEASURED VALUE | TRUE AGE − 15 ~ TRUE AGE − 12 |
| B: | PREDICTED VALUE + 1.5 SD < MEASURED VALUE < PREDICTED VALUE + 2.0 SD | TRUE AGE − 12 ~ TRUE AGE − 9 |
| C: | PREDICTED VALUE + 1.0 SD < MEASURED VALUE < PREDICTED VALUE + 1.5 SD | TRUE AGE − 9 ~ TRUE AGE − 6 |
| D: | PREDICTED VALUE + 0.5 SD < MEASURED VALUE < PREDICTED VALUE + 1.0 SD | TRUE AGE − 6 ~ TRUE AGE − 3 |
| E: | PREDICTED VALUE − 0.5 SD < MEASURED VALUE < PREDICTED VALUE + 0.5 SD | TRUE AGE − 3 ~ TRUE AGE + 3 |
| F: | PREDICTED VALUE − 1.0 SD < MEASURED VALUE < PREDICTED VALUE − 0.5 SD | TRUE AGE + 3 ~ TRUE AGE + 6 |
| G: | PREDICTED VALUE − 1.5 SD < MEASURED VALUE < PREDICTED VALUE − 1.0 SD | TRUE AGE + 6 ~ TRUE AGE + 9 |
| H: | PREDICTED VALUE − 2.0 SD < MEASURED VALUE < PREDICTED VALUE − 1.5 SD | TRUE AGE + 9 ~ TRUE AGE + 12 |
| I: | MEASURED VALUE < PREDICTED VALUE − 2.0 SD | TRUE AGE + 12 ~ TRUE AGE + 15 |

FIG. 17
CALCULATED AGE = (2.5348 − 0.58)/0.0174 = 112
INDICATED AGE = 68 + (112 − 68) × 0.2 = 77
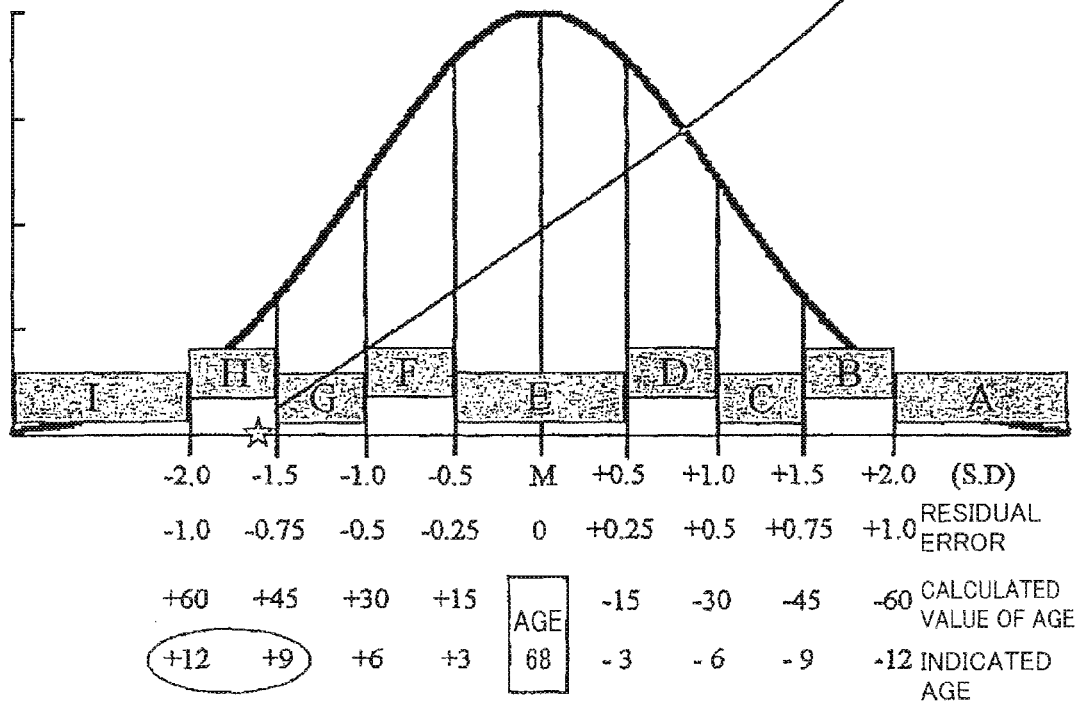
IMMUNITY-ADJUSTED AGE 68+12, 68+9
AGE 77−80

FIG. 20
|  | CASE 4 |
|---|---|
| SUBJECT AGE | 72 |
| MEASURED VALUE OF T CELL PROLIFERATION INDEX | 0.85 |
| PREDICTED VALUE OF T CELL PROLIFERATION INDEX | 1.28 |
| RESIDUAL ERROR | −0.43  |
| IMMUNITY RANK | F |
| IMMUNITY-ADJUSTED AGE / INDICATED FORM | AGE 75–78 |
CALCULATED AGE = (2.5348 − 0.85) / 0.0174 = 97
INDICATED AGE = 72 + (97 − 72) × 0.2 = 77
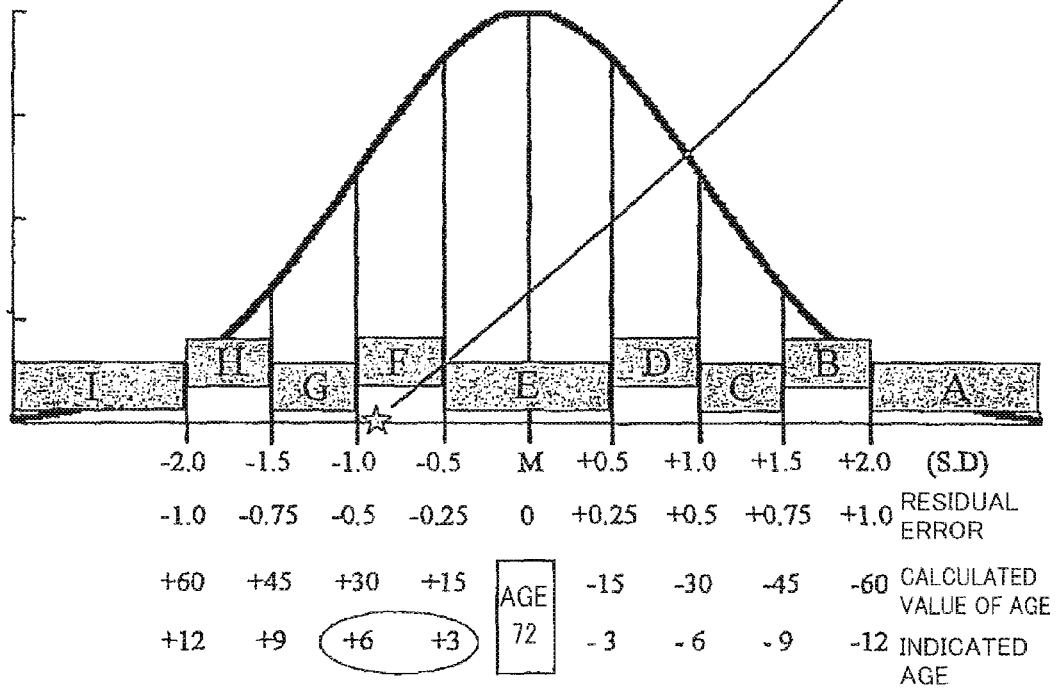
IMMUNITY-ADJUSTED AGE 72+6, 72+3
AGE 75–78

IMMUNITY-ADJUSTED AGE 3+56, 56-3
AGE 53-59

IMMUNITY EVALUATION METHOD, IMMUNITY EVALUATION APPARATUS, IMMUNITY EVALUATION PROGRAM AND DATA RECORDING MEDIUM HAVING THE IMMUNITY EVALUATION PROGRAM STORED THEREIN

CROSS-REFERENCE TO RELATED APPLICATIONS

This application is the National Stage of International Application No. PCT/JP2007/062158, filed Jun. 15, 2007, which claims the benefit of Japanese Application No. 2006-166626, filed Jun. 15, 2006, the contents of which is incorporated by reference herein.

TECHNICAL FIELD

The present invention relates to an immunity evaluation method, an immunity evaluation apparatus, an immunity evaluation program and a data recording medium storing the immunity evaluation program for evaluating immunity by using immune cell markers for a plurality of immune cells contained in sampled blood.

BACKGROUND ART

Lymphocytes in the blood are cells that play a central role in immunity, constituting cells (subsets) having different functions, such as T cells, B cells and natural killer (NK) cells. The T cells are not a uniform group of cells but include functionally differing subsets of cells which are known as CD4 T cells, CD8 T cells or naive T cells.

The individual types of cells mentioned above have surface proteins (antigens) characteristic of the respective cell types. The number and ratio of each type of cells have conventionally been determined by dyeing a monoclonal antibody of the relevant antigen and then using a flowcytometric analysis. Also, functions of individual lymphocytes used to be determined by measuring a protein (cytokine) related to proliferative activity or proliferation of the individual lymphocytes under cultural conditions.

Using the aforementioned method, the inventors of the present Application have revealed that the subset configuration of lymphocytes and functions thereof could vary or degrade as a result of aging (refer to Non-patent Documents 1 and 2).

Non-patent Document 1: "Differential age-change in the number of CD4+, CD45RA+ and CD4+CD29+ T cell subsets in the human peripheral blood", Mechanism of Ageing and Development, Utsuyama M., Hirokawa K., Kurashima C, Fukayama M., Inamatsu T., Suzuki K., Hashimoto W. and Sato K., Vol. 63-1, pp. 57-88, Mar. 15, 1992.

Non-patent Document 2: Katsuiku Hirokawa, "Aging and Immunity", Nippon Ronen Igakkai Zasshi (Journal of The Japan Geriatrics Society), vol. 40-6, pp. 543-552, November. 2003.

While individual data given in these Non-patent Documents show the ratios and functions of individual cell subsets, the data do not necessarily represent the comprehensive immunity of humans.

White blood cells exist at a concentration of 4000-8000 cells/μl in peripheral blood of a healthy person. The white blood cells include (I) granular leukocytes having segmented nuclei and neutrophilic granules and (II) mononuclear cells each having a round nucleus. Most of the mononuclear cells are lymphocytes part of which constitute monocytes (macrophages) having a function of phagocytosis. The lymphocytes made of such mononuclear cells play a major role as immune cells.

The lymphocytes are made up of various subgroups having different functions. Three larger subgroups are those of T cells, B cells and NK cells.

The T cells are further divided into two large groups called CD4 T cell and CD8 T cell subsets. Either the T cells or the B cells include memory cells which have received antigenic stimulation due to infection or the like and naive cells which have not experienced any antigenic stimulation.

While the above discussion has shown a rough grouping of the lymphocytes, these groups respectively have different functions. This means that the immunity of a human is made of total capability of the functions of various subsets having such different functions.

Therefore, a subset having one function does not represent the entirety of an individual.

As explained thus far in detail, it is possible to observe the functions of a wide variety of lymphocyte subsets and proportions thereof among the entire lymphocytes. Specifically, although it is possible to acquire cell population data, such as a T cell count of 1540 cells/μl, a B cell count of 105 cells/μl and an NK cell count of 225 cells/μl, it is not obvious how individual items of these data correlate with the immunity of a human. In other words, there is a problem that no method is available to an individual person for objectively evaluating the level of his or her own immunity (immune function).

DISCLOSURE OF THE INVENTION

In light of the foregoing, it is an object of the invention to provide an immunity evaluation method, an immunity evaluation apparatus, an immunity evaluation program and a data recording medium storing the immunity evaluation program, which make it possible to objectively evaluate immunity in a general, comprehensive fashion.

According to the present invention, an immunity evaluation method for evaluating immunity by using immune cell markers for immune cells contained in sampled blood comprises the step of determining an evaluation value for each of at least two selected kinds of immune cell markers based on the individual immune cell markers contained in the sampled blood, the step of adding the evaluation values so obtained for the at least two selected kinds of immune cell markers, and the step of evaluating the immunity from the results of the adding. Since this method evaluates a general immune function by adding up the evaluation values of a plurality of immune cell markers, it is possible to objectively evaluate the general, comprehensive immunity.

Preferably, the step of determining the evaluation value is a scoring step for executing scoring operation according to a value of each of the immune cell markers based on a specific reference value, and the step of adding is an adding step for determining a score by adding points obtained by the scoring operation. This method executes the scoring operation according to the value of each of the immune cell markers contained in the sampled blood for each of the at least two selected kinds of immune cell markers based on the specific reference value and evaluates the immunity based on the score obtained by adding the individual points. It is therefore possible to objectively evaluate the general, comprehensive immunity of each person whose blood has been sampled.

It is also preferable that the step of evaluating be an evaluation step for evaluating the immunity in a stepwise fashion by classifying immunity evaluation results into a plurality of grades according to the points and determining to which grade the score belongs. This method evaluates the immunity in a stepwise fashion by classifying the immunity evaluation results into a plurality of grades according to the points and determining to which grade the score belongs, so that it is possible to clearly evaluate the immunity.

It is also preferable that the at least two selected kinds of immune cell markers include at least two of a T cell count, a T cell proliferation index, a CD4/CD8 T cell count ratio, a naive T cell count, a naive/memory T cell count ratio, IL-2 cytokine productivity, IFN-γ cytokine productivity, IL-4 cytokine productivity, a B cell count and an NK cell count. Since this method uses at least two selected kinds of immune cell markers taken from among the T cell count, the T cell proliferation index, the CD4/CD8 T cell count ratio, the naive T cell count, the naive/memory T cell count ratio, IL-2 cytokine productivity, IFN-γ cytokine productivity, IL-4 cytokine productivity, the B cell count and the NK cell count, it is possible to evaluate high and low levels of the general, comprehensive immunity.

It is also preferable that the at least two selected kinds of immune cell markers include at least one of a T cell count and a T cell proliferation index. Since at least one of the T cell count and the T cell proliferation index is included, high and low levels of the immunity are likely to be reflected in the result of immunity evaluation.

According to the present invention, another immunity evaluation method for evaluating immunity by using a T cell proliferation index or the quantity of reexpressed CD3 detected from sampled blood comprises the step of determining in advance a regression equation based on a correlation between the T cell proliferation index or the quantity of reexpressed CD3 and age, the step of determining a predicted value of the T cell proliferation index or the quantity of reexpressed CD3 by substituting an input true age into the regression equation, and the step of determining an estimated range of immunity-adjusted age from the predicted value so obtained and the determined T cell proliferation index or the quantity of reexpressed CD3. Since the immunity is expressed in terms of age by using the T cell proliferation index or the quantity of reexpressed CD3 which is highly correlated with age, it is possible to objectively evaluate the general, comprehensive immunity.

According also to the present invention, an immunity evaluation apparatus for evaluating immunity by using immune cell markers for immune cells contained in sampled blood comprises means for determining an evaluation value for each of at least two selected kinds of immune cell markers based on the individual immune cell markers contained in the sampled blood, means for adding the evaluation values so obtained for the at least two selected kinds of immune cell markers, and means for evaluating the immunity from the results of the adding. Since this apparatus evaluates a general immune function by adding up the evaluation values of a plurality of immune cell markers, it is possible to objectively evaluate the general, comprehensive immunity.

Preferably, the means for determining the evaluation value is scoring means for executing scoring operation according to a value of each of the immune cell markers based on a specific reference value, and the means for adding is adding means for determining a score by adding points obtained by the scoring operation. This apparatus executes the scoring operation according to the value of each of the immune cell markers input through an input unit for each of the at least two selected kinds of immune cell markers based on the specific reference value and evaluates the immunity based on the score obtained by adding the individual points. It is therefore possible to objectively evaluate the general, comprehensive immunity.

It is also preferable that the immunity evaluation apparatus comprise a storage unit storing an evaluation table classifying immunity evaluation results in a stepwise form according to the points, wherein the means for evaluating is evaluation means for evaluating the immunity in a stepwise fashion by determining to which one of grades held in the evaluation table the score belongs. Since the apparatus is provided with the storage unit storing the evaluation table classifying the immunity evaluation results in a stepwise form according to the points and the evaluation means determines to which one of the grades held in the evaluation table the score belongs, it is possible to easily evaluate the immunity.

It is also preferable that the immunity evaluation apparatus have a storage unit storing a database in which immune cell marker values of a healthy person used as specific reference values for a plurality of immune cells are interrelated with information related to the healthy person. Since the apparatus has the storage unit storing the database in which the immune cell marker values of the healthy person used as the specific reference values for the plurality of immune cells are interrelated with the information related to the healthy person, it is possible to evaluate the immunity without instability.

It is also preferable that the at least two selected kinds of immune cell markers include at least two of a T cell count, a T cell proliferation index, a CD4/CD8 T cell count ratio, a naive T cell count, a naive/memory T cell count ratio, IL-2 cytokine productivity, IFN-γ cytokine productivity, IL-4 cytokine productivity, a B cell count and an NK cell count. Since the immunity evaluation apparatus uses at least two selected kinds of immune cell markers taken from among the T cell count, the T cell proliferation index, the CD4/CD8 T cell count ratio, the naive T cell count, the naive/memory T cell count ratio, IL-2 cytokine productivity, IFN-γ cytokine productivity, IL-4 cytokine productivity, the B cell count and the NK cell count, it is possible to evaluate high and low levels of the general, comprehensive immunity.

It is also preferable that the at least two selected kinds of immune cell markers include at least one of a T cell count and a T cell proliferation index. Since at least one of the T cell count and the T cell proliferation index is included, high and low levels of the immunity are likely to be reflected in the result of immunity evaluation.

According to the present invention, another immunity evaluation apparatus for evaluating immunity by using a T cell proliferation index or the quantity of reexpressed CD3 detected from sampled blood comprises means for determining in advance a regression equation based on a correlation between the T cell proliferation index or the quantity of reexpressed CD3 and age, means for determining a predicted value of the T cell proliferation index or the quantity of reexpressed CD3 by substituting an input true age into the regression equation, and means for determining an estimated range of immunity-adjusted age from the predicted value so obtained and the determined T cell proliferation index or the quantity of reexpressed CD3. Since the immunity is expressed in terms of age by using the T cell proliferation index or the quantity of reexpressed CD3 which is highly correlated with age, it is possible to objectively evaluate the general, comprehensive immunity.

According also to the present invention, an immunity evaluation program for realizing functions on a computer to evaluate immunity by using immune cell markers for immune cells contained in sampled blood is so configured as to realize the function of determining an evaluation value for each of at least two selected kinds of immune cell markers based on the individual immune cell markers input through an input unit, the function of adding the evaluation values so obtained for the at least two selected kinds of immune cell markers, and the function of evaluating the immunity from the results of the adding. Since this program evaluates a general immune function by adding up the evaluation values of a plurality of immune cell markers, it is possible to objectively evaluate the general, comprehensive immunity.

Preferably, the function of determining the evaluation value is a scoring function of executing scoring operation according to a value of each of the immune cell markers based on a specific reference value, and the function of adding is an adding function of determining a score by adding points obtained by the scoring operation. This program executes the scoring operation according to the value of each of the immune cell markers input through an input unit for each of the at least two selected kinds of immune cell markers based on the specific reference value and evaluates the immunity based on the score obtained by adding the individual points. It is therefore possible to objectively evaluate the general, comprehensive immunity.

It is also preferable that the function of evaluating be an evaluation function of evaluating the immunity in a stepwise fashion by determining to which one of grades held in an evaluation table classifying immunity evaluation results in a stepwise form according to the points the score belongs. Since the program is provided with the evaluation table classifying the immunity evaluation results in a stepwise form according to the points and the evaluation function evaluates the immunity in a stepwise fashion by determining to which one of the grades held in the evaluation table the score belongs, it is possible to easily evaluate the immunity.

According to the present invention, another immunity evaluation program for realizing functions on a computer to evaluate immunity by using a T cell proliferation index or the quantity of reexpressed CD3 detected from sampled blood is so configured as to realize the function of determining in advance a regression equation based on a correlation between the T cell proliferation index or the quantity of reexpressed CD3 and age, the function of determining a predicted value of the T cell proliferation index or the quantity of reexpressed CD3 by substituting an input true age into the regression equation, and the function of determining an estimated range of immunity-adjusted age from the predicted value so obtained and the determined T cell proliferation index or the quantity of reexpressed CD3. Since the immunity is expressed in terms of age by using the T cell proliferation index or the quantity of reexpressed CD3 which is highly correlated with age, it is possible to objectively evaluate the general, comprehensive immunity.

A data recording medium of the present invention readable by a computer stores one of the aforementioned immunity evaluation programs.

BRIEF DESCRIPTION OF THE DRAWINGS

FIG. 3 is an explanatory diagram showing immune cell marker values of healthy persons having no disease;

FIG. 6 is an evaluation table obtained by classifying immunity evaluation results in stepwise form according to scores thereof;

FIG. 10 is an explanatory diagram showing the individual immune cell markers and a specific example of points assigned thereto;

FIG. 15 is a flowchart for explaining an example of an immunity evaluation process performed by the main computer unit;

FIG. 16 is a diagram showing an evaluation table representing immunity evaluation classification of measured values and predicted values of T cell proliferation indices and immunity-adjusted ages;

FIG. 17 is a diagram showing immunity evaluation classification and an immunity-adjusted age determined for a particular sample;

FIG. 20 is a diagram showing immunity evaluation classification and an immunity-adjusted age determined for another particular sample;

PREFERRED MODE FOR CARRYING OUT THE INVENTION

Figure 1:
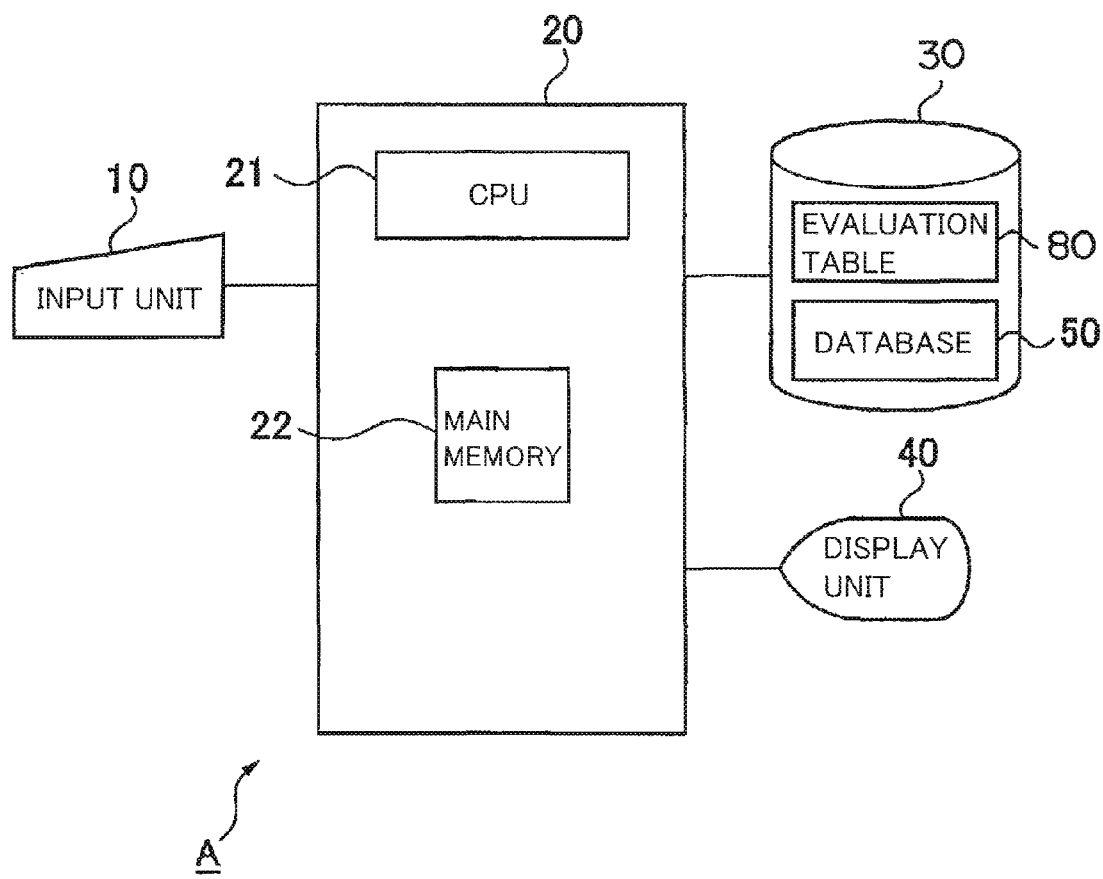
FIG. 1 is a block diagram showing the overall structure of an immunity evaluation apparatus according to one embodiment of the present invention.
Figure 2:
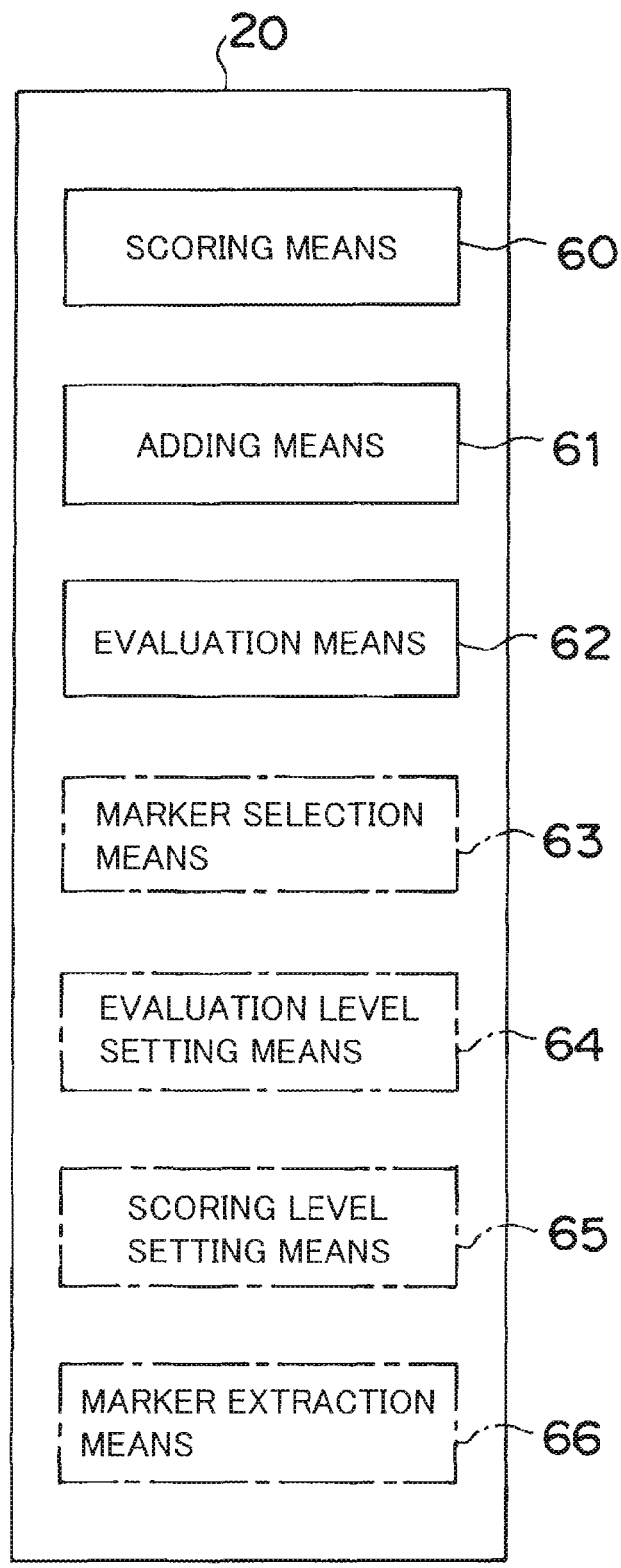
FIG. 2 is a block diagram showing functions possessed by a main computer unit.

Best modes for carrying out the present invention are now described with reference to the drawings. FIG. 1 is a block diagram showing the overall structure of an immunity evaluation apparatus according to one embodiment of the present invention, FIG. 2 is a block diagram showing functions possessed by a main computer unit, and FIG. 3 is an explanatory diagram showing values of immune cell markers of healthy persons having no disease.

As shown in FIG. 1, the immunity evaluation apparatus A according to the embodiment of the present invention is built up mainly of a digital computer including an input unit 10, the main computer unit 20, an external storage device 30 constituting a storage unit, a display unit 40, and so on.

The input unit 10 includes a keyboard and a mouse, for example, through which information related to persons subjected to immunity evaluation (i.e., persons whose blood has been sampled), later-described immune cell marker values and information related to healthy persons, and so on, can be input.

The aforementioned "information related to persons subjected to immunity evaluation" includes the name, address, sex, age, past illnesses, present illnesses, and so on, of each person subjected to immunity evaluation.

The main computer unit 20 mainly includes, in addition to a central processing unit (CPU) 21, a main memory 22, an interface circuit (not shown) for establishing a connection with an external circuit, and so on.

The external storage device 30 is a hard disk drive, for example, storing a database 50, an evaluation table 80, and so on, together with a later-described immunity evaluation program, of which contents are read out into the main memory 22 of the main computer unit 20 and executed where necessary.

The database 50 is for storing data on immune cell marker values of a healthy person used as specific reference values for a plurality of immune cells and information related to the healthy person in an interrelated manner. The database 50 is so configured that immune cell marker values of a new healthy person can be additionally stored when appropriate through the aforementioned input unit 10.

A "healthy person" is a person who has been found to have no specific anomalies in a general medical examination, and the "information related to healthy persons" includes the name, address, sex, age, weight, height, and so on, of each healthy person.

The immunity evaluation program is a program programmed using a known programming language that causes the main computer unit to operate based on an immunity evaluation method according to the present embodiment described hereinbelow. This program, when executed, provides the main computer unit 20 with a function of scoring means 60, a function of adding means 61, a function of immunity evaluation means 62, a function of marker selection means 63, a function of evaluation level setting means 64, a function of score level setting means 65 and a function of marker extraction means 66 as shown in FIG. 2. The individual functions will be described later in great detail.

The immunity evaluation method of the present embodiment is intended in essence to evaluate immunity by using immune cell markers for a plurality of immune cells contained in blood samples. Specifically, the immunity evaluation method scores the immunity according to values of the individual immune cell markers for each of preselected at least two immune cell markers based on the specific reference values and evaluates the immunity based on a score obtained by adding up individual points given as a result of scoring.

In this embodiment, the immunity is scored in a stepwise fashion according to the values of the individual immune cell markers for each of preselected at least two immune cell markers based on the specific reference values and evaluated stepwise based on the score obtained by adding up the results of scoring.

The "immune cell markers" referred to herein are those for a plurality of immune cells contained in the blood samples.

Used in this embodiment are 10 kinds of immune cell markers which are appropriate for immune cells contained in lymphocytes within peripheral blood.

As shown in FIG. 3, the 10 kinds of immune cell markers are (a) the number of T cells per microliter (T cell count), (b) T cell proliferation index, (c) CD4/CD8 T cell count ratio, (d) the number of naive T cells per microliter (naive T cell count), (e) naive/memory T cell count ratio, (f) the number of B cells per microliter (B cell count), (g) the number of natural killer (NK) cells per microliter (NK cell count), (h) IL-2 cytokine productivity, (i) IFN-γ cytokine productivity and (j) IL-4 cytokine productivity. The immune cell markers are not however limited to these 10 kinds but other kinds of immune cell markers may be adopted instead.

While (h) IL-2 cytokine productivity, (i) IFN-γ cytokine productivity and (j) IL-4 cytokine productivity are functions of the immune cells, the "immune cell markers" are meant to include these functions as well in the present embodiment.

Also, while the following discussion of the present embodiment deals with the number of T cells per microliter or the like, it goes without saying that the cell population can be expressed by the number of cells per any unit of fluid.

All of the 10 kinds of immune cell markers, such as (a) the number of T cells per microliter and (b) T cell proliferation index, are selected in the present embodiment. When at least two kinds of immune cell markers are to be selected, however, it is preferable that the immune cell markers be selected in the following combinations.

Specifically, when two kinds of immune cell markers are to be combined, the immune cell markers should be selected to include at least one of T cell count and T cell proliferation index. Preferably, the immune cell markers should be selected to include both (a) the number of T cells per microliter and (b) T cell proliferation index.

Also, when three or more kinds of immune cell markers are to be selected, the immune cell markers should preferably be selected to include both (a) the number of T cells per microliter and (b) T cell proliferation index in the same way as mentioned above. If the immune cell markers are selected in the aforementioned combinations, variations in immunity are likely to be reflected in the result of immunity evaluation and the immunity (immune function) can be evaluated in a general, comprehensive fashion.

The (b) T cell proliferation index is a totally novel conceptual value capable of reflecting both T cell count and T cell proliferative activity and can be expressed by the following equation:

$$(T\text{ cell proliferation index}) = \text{OD (490 nm) value} \times (\text{number of } T \text{ cells per microliter}/1000)$$

While the number of T cells per microliter is divided by 1000 in the above equation, this is for matching the number of digits with other values shown in FIG. 3 and the number of T cells per microliter need not necessarily be divided by 1000.

The OD (optical density) value is the value of absorbance which reflects the proliferative activity of T cells. In this embodiment, the OD value is calculated by MTS method without using any isotope. The value 490 (nm) shown above in parentheses is the wavelength of light.

Given below is an outline of the MTS method:

"CellTiter 96 (registered trademark) AQueous One Solution Cell Proliferation Assay" is a reagent used for colorimetric analysis for measuring (counting) the number of live cells in a cell proliferation test or a toxicological cell test.

The reagent contains a new tetrazolium compound named "3-(4,5-dimethylthiazol-2-yl)-5-(3-carboxymethoxyphenyl)-2-(4-sulfophenyl)-2H-tetrazolium, inner salt (MTS)" and a electron capturing agent named "phenazine ethosulfate (PES)". Since PES stabilizes under coexistence with MTS (tetrazolium salt), it is possible to produce a convenient single solution.

CellTiter 96(R) AQueous One Solution Assay can decrease analysis time compared to other tetrazolium compounds, such as methyl-thiazole-tetrazolium (MTT) or iodo-nitro-tetrazolium (INT). This is because this product is supplied as a stable single solution and it is not necessary to solubilize an MTS formazan product. In treatment of an assay, a small quantity of CellTiter 96 AQueous One Solution Reagent is directly added to a culture well and the assay is incubated for a period of 1-4 hours. MTS (Owen's Reagent) is reduced by live cells and converted into a colored formazan product which is soluble in the culture. Measurement can easily be made if carried out at 490 nm by using the 96-well plate reader. Formazan values measured at 490 nm are proportional to the number of live cells in the culture. This product can be used as a substitute for the [$^3$H]-thymidine incorporation method.

As the T cell proliferation index can be calculated without using any isotope as mentioned above, it is possible to easily implement the present invention at a clinic or the like having no expensive facilities for conducting nuclear medical examinations.

The immunity evaluation program of the present invention is so configured as to cause the computer to perform a scoring function for scoring the immunity according to values of the individual immune cell markers for each of preselected at least two immune cell markers based on the specific reference values and an immunity evaluation function for evaluating the immunity based on a score obtained by adding up individual points.

In this embodiment, the digital computer serves the scoring function to score the immunity in a stepwise fashion according to the values of the individual immune cell markers for each of preselected at least two immune cell markers based on the specific reference values as well as the immunity evaluation function to evaluate the immunity stepwise based on the score obtained by adding up individual points.

The "digital computer" herein referred to is equivalent to the immunity evaluation apparatus A in this embodiment.

While the immunity evaluation program is stored in the external storage device 30, the invention is not limited to this structure but the immunity evaluation program may be recorded in any of various information storage media, such as a portable magnetic disk, a magneto-optic disk and a semiconductor memory. This means that an arrangement may be made such that the immunity evaluation program can be installed when the need arises. If the immunity evaluation program is recorded in a portable data recording medium, the immunity evaluation program can easily be upgraded to an improved version.

The immunity evaluation program may be recorded in the data recording medium not only in a readily executable form but in a compressed or encrypted form.

The main computer unit 20, and thus the immunity evaluation apparatus A, exhibits the following functions by executing the aforementioned immunity evaluation program.
(1) A function to score the immunity according to individual immune cell marker values for each of selected at least two immune cell markers based on the specific reference values (scoring means 60).

In the present embodiment, this function scores the immunity in a stepwise fashion according to the individual immune cell marker values based on the specific reference values for the group of the aforementioned 10 kinds of immune cell markers.

The "specific reference values" are immune cell marker values of healthy persons which are the values shown specifically in FIG. 3.

The expression "scores the immunity in a stepwise fashion according to the individual immune cell marker values" means that the immune cell marker values of the healthy persons are classified into three levels including a range of cumulative frequencies of less than 10%, a range of cumulative frequencies of 10% or more but less than 40%, and a range of cumulative frequencies of 40% or more, and progressively smaller points are assigned to the individual levels as the immunity decreases. Due to such classification of the immune cell marker values into the three discrete levels according to the cumulative frequency, it is possible to score the immunity in a reliable fashion.

To be more specific, using values at the cumulative frequency of 10% and at the cumulative frequency of 40% as references, 1 point is assigned to values with a cumulative frequency of 10%, 2 points are assigned to values with a cumulative frequency of 10% or more but less than 40%, and 3 points are assigned to values with a cumulative frequency of 40% or more.

Specifically, values of the healthy persons within the range of cumulative frequencies of less than 10% are assigned 1 point indicating a low immunity level, values within the range of cumulative frequencies of 10% or more but less than 40% are assigned 2 points indicating a medium immunity level, and values within the range of cumulative frequencies of 40% or more are assigned 3 points indicating a sufficiently high immunity level.

In short, a larger number of points are assigned to higher immunity levels while a smaller number of points are assigned to lower immunity levels.

While the present embodiment is described by using an example in which 1, 2 or 3 points are assigned to the three individual levels, the invention is not limited to this arrangement but should only be such that higher immunity levels are assigned correspondingly higher points and lower immunity levels are assigned correspondingly lower points.

It is to be noted that the aforementioned criteria of the cumulative frequency of 10% and the cumulative frequency of 40% would more or less vary as the number of healthy persons accumulated in the database 50 increases.

Figure 4:
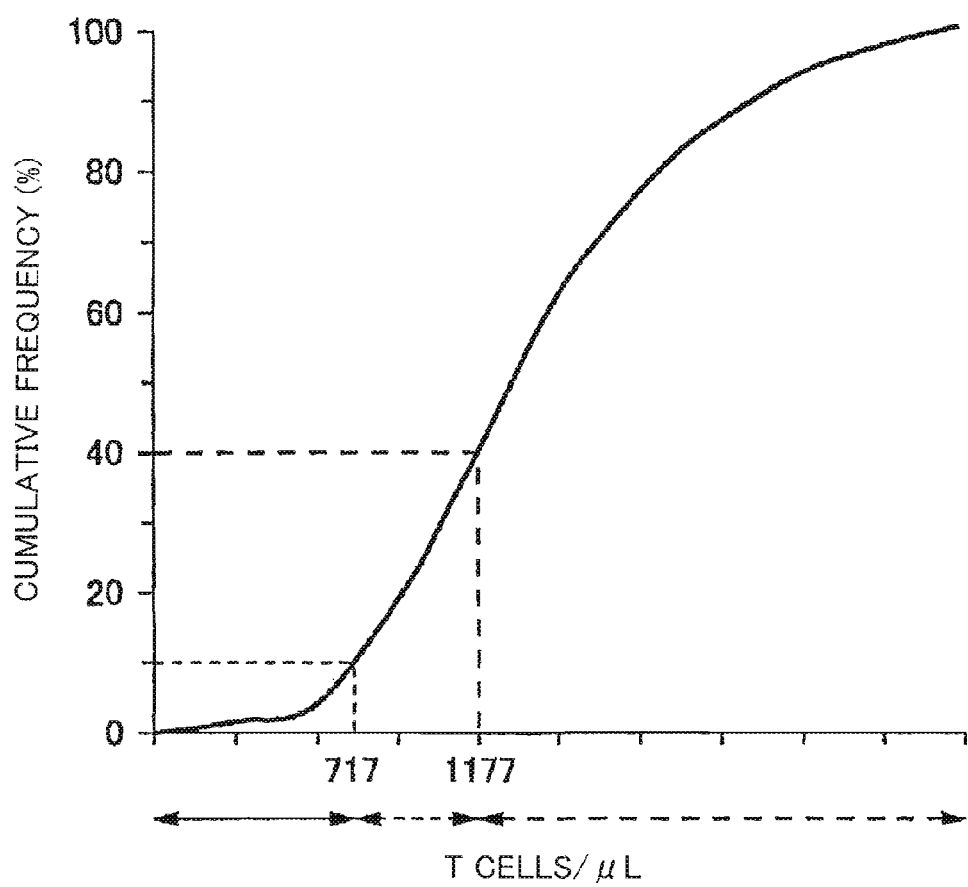
FIG. 4 is a diagram showing a relationship between T cell count and cumulative frequency.
Figure 5:
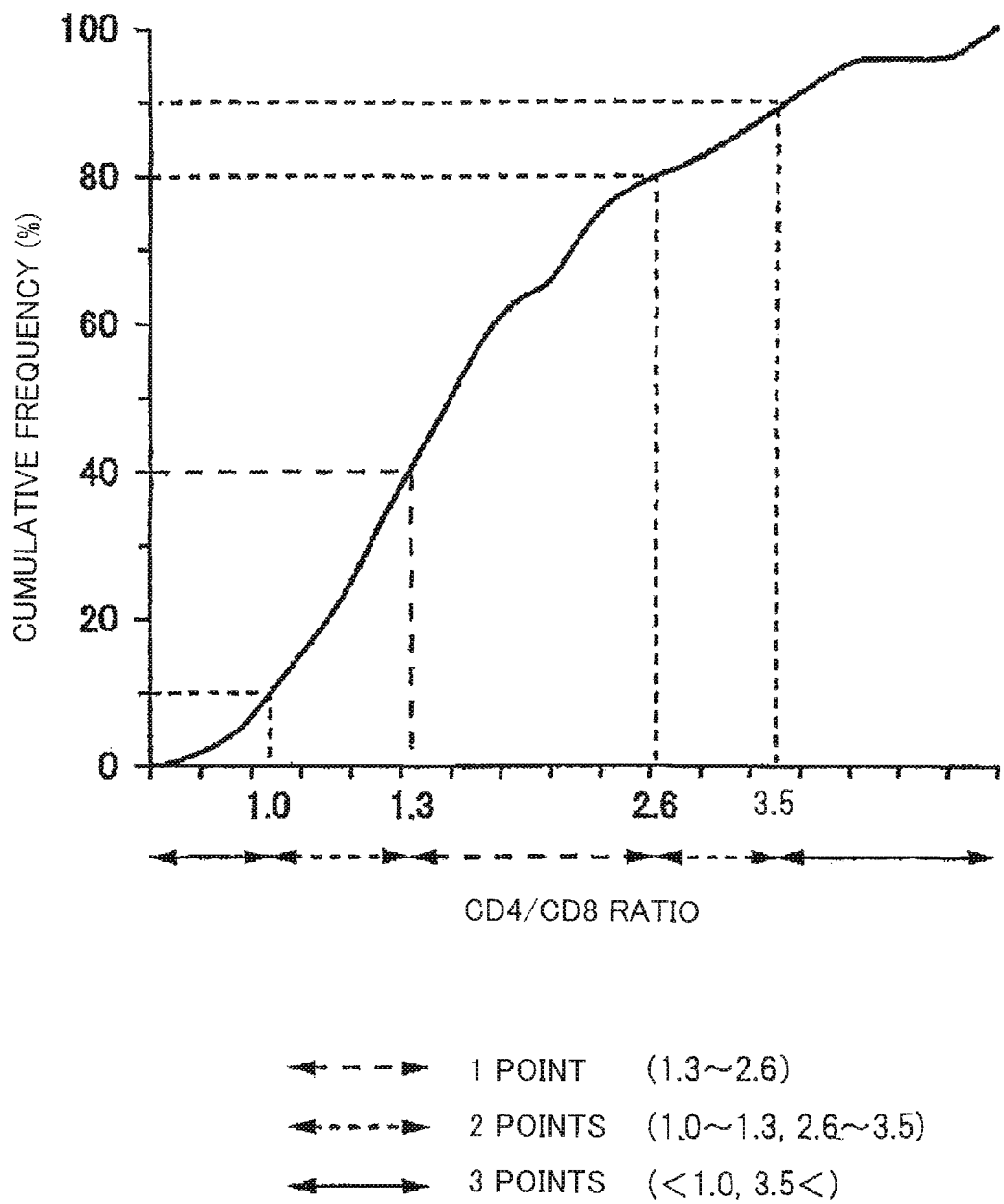
FIG. 5 is a diagram showing a relationship between CD4/CD8 T cell count ratio and cumulative frequency.

A specific scoring scheme is now described by using an example in which the T cell count and the CD4/CD8 T cell count ratio are selected from among the aforementioned immune cell markers, for example. FIG. 4 is a diagram showing a relationship between the T cell count and the cumulative frequency, and FIG. 5 is a diagram showing a relationship between the CD4/CD8 T cell count ratio and the cumulative frequency.

As depicted in FIG. 4, the T cell count of peripheral blood corresponding to the cumulative frequency of 10% is 717, so that 1 point is given if the T cell count of the sampled peripheral blood is less than 717.

Also, the T cell count of peripheral blood corresponding to the cumulative frequency of 40% is 1177, so that 2 points are given if the T cell count is 717 or greater, or less than 1177. Similarly, 3 points are given if the T cell count is 1177 or greater.

The CD4/CD8 T cell count ratio is scored as follows in a manner different from what is used for the other immune cell markers including the aforementioned T cell count.

As depicted in FIG. 5, the CD4/CD8 T cell count ratio corresponding to the cumulative frequency of 10% is 1.0, the CD4/CD8 T cell count ratio corresponding to the cumulative frequency of 40% is 1.3, and the CD4/CD8 T cell count ratio corresponding to a cumulative frequency of 80% is 2.6.

Further, 1 point is assigned to a value falling within the range of cumulative frequencies of less than 10%, 2 points are assigned to a value falling within the range of cumulative frequencies of 10% or more but less than 40%, 3 points are assigned a value falling within a range of cumulative frequencies of 40% or more but less than 80%, 2 points are assigned to a value falling within a range of cumulative frequencies of 80% or more but less than 90%, and 1 point is assigned to a value falling within a range of cumulative frequencies of 90% or more.

Specifically, 1 point is assigned if the CD4/CD8 T cell count ratio is less than 1.0, 2 points are assigned if the CD4/CD8 T cell count ratio is 1.0 or higher but less than 1.3, 3 points are assigned if the CD4/CD8 T cell count ratio is 1.3 or higher but less than 2.6, 2 points are assigned if the CD4/CD8 T cell count ratio is 2.6 or higher but less than 3.5, and 1 point is assigned if the CD4/CD8 T cell count ratio is 3.5 or higher to score individual values of the CD4/CD8 T cell count ratio.

A reason why 2 points are assigned to a CD4/CD8 T cell count ratio corresponding to a cumulative frequency of 80% or more but less than 90% and 1 point is assigned to a CD4/CD8 T cell count ratio corresponding to a cumulative frequency of 90% or more is that the CD4/CD8 T cell count ratio has a tendency to increase with aging.

(2) A function to evaluate the immunity stepwise based on a score obtained by adding individual points (adding means 61 and evaluation means 62).

FIG. 6 is an evaluation table obtained by classifying immunity evaluation results in a stepwise form according to gained points. The evaluation table 80 obtained by arranging this evaluation table in a tabular form is stored in the external storage device 30.

Specifically, this function evaluates the immunity stepwise by determining to which range each score belongs referring to the evaluation table 80 corresponding to the evaluation table (A) obtained by stepwise classification of the immunity evaluation results.

The evaluation table (A), or the evaluation table 80, is configured in the following fashion.

A total point obtained by adding up points assigned to the aforementioned 10 kinds of immune cell markers exists between 30 and 10.

Thus, the results of immunity evaluation are classified into 5 grades corresponding to the total point.

The individual grades (hereinafter referred to as "grades") are classified as follows:

Grade 5: Corresponds to a range of 30-29 points, indicating that a subject has sufficiently high immunity.

Grade 4: Corresponds to a range of 28-26 points, indicating that a subject has high immunity.

Grade 3: Corresponds to a range of 22-25 points, indicating that a subject has ordinary immunity or immunity in a stage of initial degradation.

Grade 2: Corresponds to a range of 21-17 points, indicating that a subject has slightly degraded immunity.

Grade 1: Corresponds to a range of 16-10 points, indicating that a subject has highly degraded immunity.

Grade 5 is the range containing 2 different numbers of total points, grade 4 is the range containing 3 different numbers of total points, grade 3 is the range containing 4 different numbers of total points, grade 2 is the range containing 5 different numbers of total points, and grade 1 is the range containing 7 different numbers of total points.

The lower the grade, the wider the range of points. This is because the grade of healthy persons rarely drops to grade 2 or 1, whereas persons having diseases, such as cancerous patients who exhibit dramatic changes in immunity, are likely to be classified as one of the lower grades.

Most of the healthy persons are distributed within grades 5 to 3. On the other hand, patients having diseases are distributed within grades 4 to 2 in most cases, and those classified in grade 1 are evaluated to be in a considerably dangerous situation.

Figure 7:
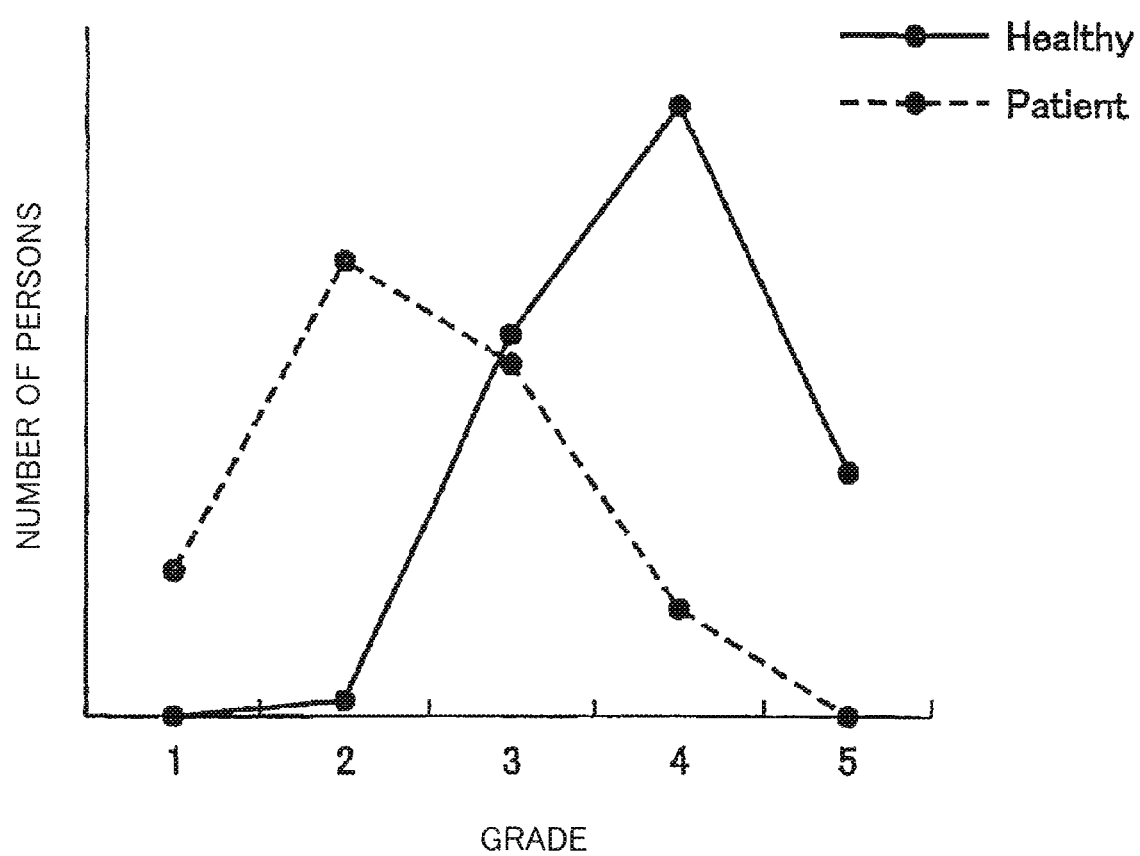
FIG. 7 is a graph showing a relationship between the number of persons and grades.

The inventors have obtained data shown in FIG. 7 as a result of experiments actually conducted on 60 healthy persons and 30 cancerous patients with their immunity classified into 5 grades. FIG. 7 is a graph showing the relationship between the number of persons and grades, in which the vertical axis represents the number of persons and the horizontal axis represents the grade.

As is apparent from FIG. 7, the healthy persons are classified in grade 3 or higher grades, whereas the cancerous patients are mostly classified in grade 3 or lower grades, exhibiting a peak in grade 2. It can be seen from above that a person having a disease exhibits obvious downgrading and those classified in grade 2 or below require care to be taken to prevent infection.

While the foregoing discussion has dealt with an example in which the 10 kinds of immune cell markers are preselected, the immune cell markers need not necessarily be preselected by may be selected in a manner described below.

(3) A function to select at least two kinds of immune cell markers (marker selection means 63).

Specifically, the aforementioned 10 kinds of immune cell markers are presented in a readily selectable form on the display unit 40 and a desired immune cell marker displayed on-screen is selected by manipulating the input unit 10, such as by pressing an enter key.

These immune cell markers may be selected in a combination corresponding to a disease or in a combination corresponding to age (aging).

An example of the "combination corresponding to a disease" may be a combination of immune cell markers of which values are apt to vary due to the relevant disease, for instance. Also, an example of the "combination corresponding to age (aging)" may be a combination of immune cell markers which are likely to vary with aging.

In a case where such kind of marker selection means 62 is provided, the scoring means is to perform stepwise scoring operation according to individual immune cell marker values for each of the selected at least two immune cell markers based on the specific reference values.

The immunity evaluation apparatus A may be configured to have the following functions in addition to the aforementioned functions (1)-(3).

(4) A function to set an increased or decreased number of grades of immunity evaluation results (evaluation level setting means 64).

While the embodiment has been discussed thus far with reference to an example in which the number of grades of immunity evaluation results is set to 5, the number of grades of immunity evaluation results may be increased or decreased in a manner described below.

In Case of Subjects Like Cancerous Patients Having Disease

The number of grades of immunity evaluation results is increased by subdividing grades 2 and 1. For example, grades 2 and 1 are each subdivided into 3 grades to obtain a total of 9 grades.

An arrangement for increasing and decreasing the number of grades may be such that an evaluation table for the aforementioned 5 grades and an evaluation table for the 9 grades are prepared in advance and these evaluation tables are automatically switched when past illness of each person whose blood has been sampled is input through the input unit 10, for example. This arrangement makes it possible to flexibly cope with specific diseases.

In Case of Aging

If the age is less than 50, the immunity is scored in a stepwise fashion according to individual immune cell marker values for each of 3 kinds of immune cell markers based on the specific reference values, for example, and if the age is 50 or above, the immunity is scored in a stepwise fashion according to individual immune cell marker values for each of 10 kinds of immune cell markers based on the specific reference values.

An arrangement usable in this case is such that an evaluation table for the group of the 3 kinds of immune cell markers and an evaluation table for the group of the 10 kinds of immune cell markers are prepared in advance and these reference tables are switched by judging whether the input age is 50 or above when the age of each person whose blood has been sampled is input through the input unit 10, for example.

(5) A function to set an increased or decreased number of grades of scoring results (score level setting means 65).

This function is intended to score the immunity into one of three grades mentioned above if the age is less than 50 and into one of five grades if the age is 50 or above, for example.

This kind of score level setting can be made by judging whether the input age is 50 or above when the age is input through the input unit 10, for example.

It is also possible to switch the number of grades in which results are scored from the aforementioned 3-grade scoring to 5-grade scoring when a specific past illness like that of cancerous patients is input through the input unit 10. Such a judgment may be made by judging whether a specific past illness has been input.

(6) A function to extract immune cell marker values of healthy persons based on information related to the healthy persons (marker extraction means 66).

For example, an image prompting for entry of ages or the like of persons whose immune cell marker values are to be extracted is displayed on the display unit 40, and an operator inputs specific ages through the input unit 10 in accordance with the on-screen image.

This makes it possible to use the immune cell marker values of healthy persons extracted for the individual ages as specific reference values so that the immunity can be evaluated in consideration of degradation thereof occurring in the course of aging.

The immune cell marker values of healthy persons may be extracted according to sex alone or a combination of age and sex.

Figure 8:
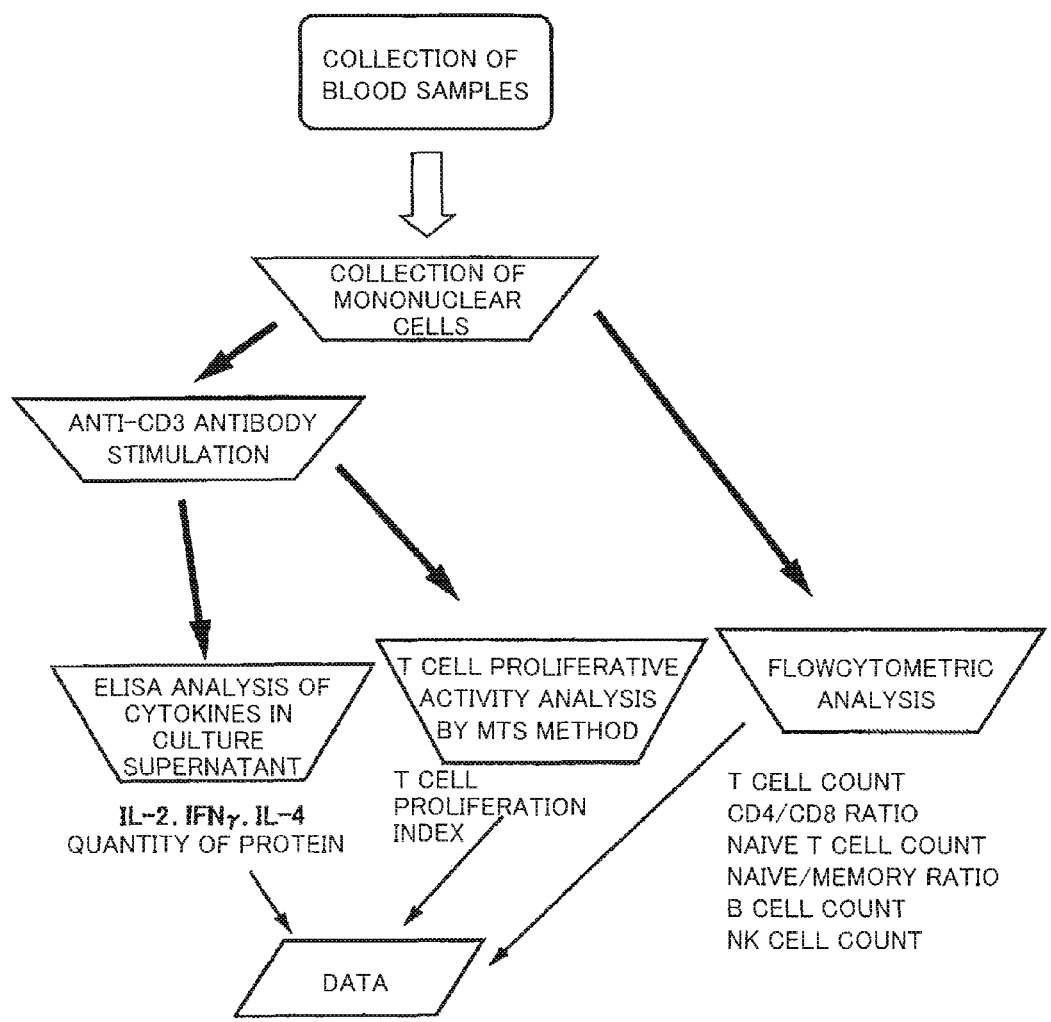
FIG. 8 is an explanatory diagram showing a procedure from the point of blood sample collection to the point of acquiring data used for calculating 10 kinds of immune cell markers.

Next, a procedural flow from collection of blood samples to immunity evaluation is described. FIG. 8 is an explanatory diagram showing a procedure from the point of blood sample collection to the point of acquiring data used for calculating the 10 kinds of immune cell markers.

As shown in this Figure, the immune cell markers or the data used for calculating the immune cell markers are acquired by collecting mononuclear cells from the blood samples and performing a flowcytometric analysis, a T cell proliferative activity analysis by the MTS method and an enzyme-linked immunosorbent assay (ELISA) analysis of cytokines in culture supernatant and, then, these data are input through the input unit 10.

Collection of Mononuclear Cells

A collection process for collecting mononuclear cells contained in blood is as follows:

1. 8 ml of a blood sample is collected in a CPT mononuclear cell preparation vacuum tube (Becton, Dickinson and Company: 8362761).
2. The blood sample is centrifuged at 3000 rpm for 20 minutes at room temperature.
3. A layer of mononuclear cells obtained by centrifugation is collected.
4. Physiological saline is added to the collected mononuclear cells layer.
5. The collected mononuclear cells are centrifuged at 1500 rpm for 10 minutes at room temperature.
6. Supernatant is discarded and physiological saline is added again.
7. The collected mononuclear cells are centrifuged at 1200 rpm for 5 minutes at room temperature.
8. Supernatant is discarded and cell culture fluid (RPMI-1640) is added to produce a cell suspension.
9. Cell concentration is measured (by using 0.2% trypan-blue solution).
10. The cell concentration is adjusted to $1 \times 10^6$ cells/ml in the cell suspension.

Flowcytometric Analysis

The flowcytometric analysis is carried out by using the collected mononuclear cells.

1. 300 µl of the cell suspension having the cell concentration of $1 \times 10^6$ cells/ml is added to 3 ml of 0.83% $NH_4Cl$ solution and stirred therein. Then, the solution is left for 3 minutes to dissolve red blood cells.
2. A 2% FBS-PBS solution is added and the sample is centrifuged at 1500 rpm for 5 minutes.
3. Supernatant is removed by suction.
4. 300 µl of the 2% FBS-PBS solution is added to resuspend the cells to thereby regulate the cell suspension.
5. 50 µl of the cell suspension is each injected in four test tubes (BD: 352002).
6. A fluorescent-labeled monoclonal antibody solution is added to the test tubes.
   a) FITC-CD20/PE-CD3
   b) FITC-CD4/PE-CD8
   c) FITC-CD4/PE-CD8/ECD-CD45RA
   d) FITC-CD16/PE-CD56
7. The test tubes are left in a dark place for 30 minutes.
8. 400 µl of the 2% FBS-PBS solution is added to regulate cells for the flowcytometric analysis.
9. A fluorescent-labeled monoclonal antibody positive cell index is calculated by a flowcytometer having dedicated software installed therein.

The above-described flowcytometric analysis makes it possible to obtain 6 kinds of immune cell markers, that is, the T cell count, the CD4/CD8 T cell count ratio, the naive T cell count, the naive/memory T cell count ratio, the B cell count and the NK cell count.

Anti-CD3 Monoclonal Antibody Stimulation

Anti-CD3 monoclonal antibody is coated on 96- and 24-well plates.

1. 30 µl of Orthoclone OKT3 solution (ORTHO BIOTECH: 672,993,402) is diluted by adding 10 ml of physiological saline.

2. The diluted OKT3 solution is supplied to the 96- and 24-well plates in quantities of 100 µl/well and 400 µl/well, respectively.

3. The samples are left at rest for 2 hours at room temperature.

4. The diluted OKT3 solution is discarded by suction and physiological saline is supplied to the 96- and 24-well plates in quantities of 200 µl/well and 1000 µl/well, respectively.

5. Physiological saline is discarded by suction and, again, physiological saline is supplied to the 96- and 24-well plates in quantities of 200 µl/well and 1000 µl/well, respectively.

6. This operation is repeated a total of 5 times.

7. Physiological saline is supplied to the 96- and 24-well plates in quantities of 200 µl/well and 2000 µl/well, respectively, and the 96- and 24-well plates are refrigerated and held until subjected to analysis.

T Cell Proliferative Activity Analysis by MTS Method 1. 10% FBS-RPM and the cell suspension having the cell concentration of $1 \times 10^6$ cells/ml are supplied to the 96-well plate prepared with the aforementioned anti-CD3 monoclonal antibody coating in quantities of 100 µl/well and 100 µl/well, respectively. Three wells are used for each sample.

2. The samples are cultured in an incubator under conditions of 5% carbon dioxide gas at 37° C.

3. At a point of 68-hour culturing, an MTS solution is added in a quantity of 40 µl/well.

4. At a point of 72-hour culturing, the samples are measured by a colorimeter (490 nm). As a consequence, it becomes possible to calculate the aforementioned T cell proliferation index.

ELISA Analysis of Cytokines in Culture Supernatant

ELISA stands for enzyme-linked immunosorbent assay which is a method of measuring antibodies or peptides, for instance, in a qualitative manner by using antigen-antibody reaction. As discussed heretofore, an antigen (e.g., a fluid sample or serum containing the antigen to be measured) is added to the measurement plates coated in advance with a specific antibody (thus forming a solid layer) appropriate for the antigen (i.e., a substance to be measured), and the antigen labeled with a color development enzyme is further added to cause an antigen-antibody reaction. After removing an excess part of the antibody which has not produced the reaction, the enzyme causes a matrix to develop a color and a resultant pigment density is detected as representative of the amount of the antigen. As a consequence, it is possible to measure the IL-2 cytokine productivity, the IFN-γ cytokine productivity and the IL-4 cytokine productivity.

Evaluation of Immunity Based on a Plurality of Immune Cell Markers

Figure 9:
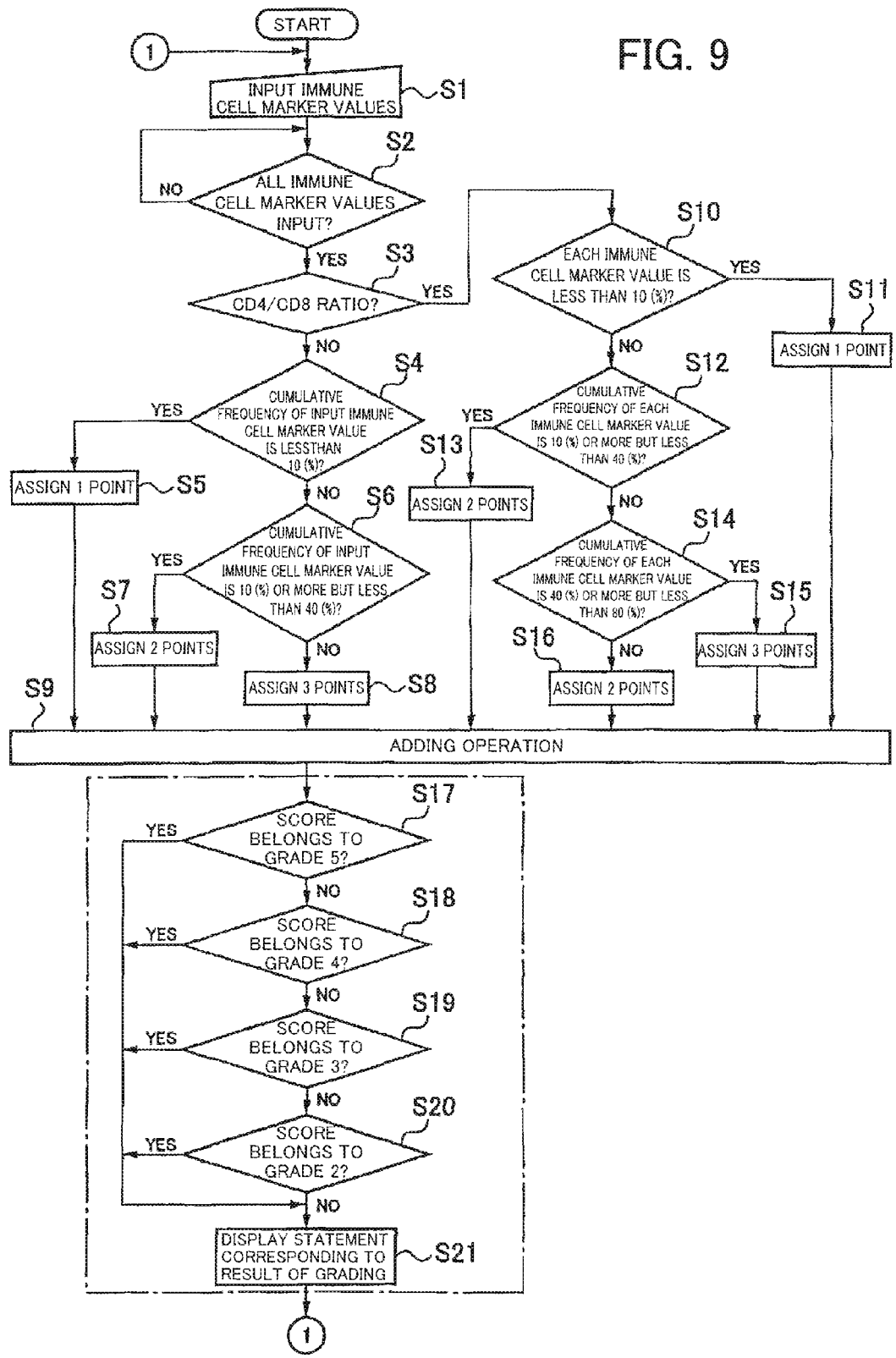
FIG. 9 is a flowchart for explaining an example of an immunity evaluation process performed by the main computer unit based on immune cell marker values input through an input unit.

FIG. 9 is a flowchart for explaining an example of an immunity evaluation process performed by the main computer unit 20 based on immune cell marker values input through the input unit 10.

Step S1: The information related to persons subjected to immunity evaluation, such as the address, name, age, sex, past illnesses, present illnesses, and so on, of each person, as well as the values of the 10 kinds of immune cell markers obtained by the aforementioned analyses and the information related to the healthy person are input through the input unit 10. The main computer unit 20 proceeds to step S2 when the enter key is pressed.

Step S2: The main computer unit 20 judges whether all of the immune cell marker values have been input and, if all of the values are judged to have been input, the main computer unit 20 proceeds to step S3.

Step S3: The main computer unit 20 judges whether the immune cell marker input through the input unit 10 is the CD4/CD8 T cell count ratio. If the result is in the affirmative, the main computer unit 20 proceeds to step S10, and if not, the main computer unit 20 proceeds to step S4.

Step S4: If the immune cell marker input through the input unit 10 is a cumulative frequency of less than 10%, the main computer unit 20 proceeds to step S5, in which the main computer unit 20 assigns 1 point to the immune cell marker and proceeds to step S9. If the immune cell marker is not a cumulative frequency of less than 10%, however, the main computer unit 20 proceeds to step S6.

Step S6: The main computer unit 20 judges whether the immune cell marker input through the input unit 10 is a cumulative frequency of 10% or more but less than 40%. If the result is judged to be affirmative, the main computer unit 20 proceeds to step S7, and if not, the main computer unit 20 proceeds to step S8.

Step S7: The main computer unit 20 proceeds to step S9 after assigning 2 points to the pertinent immune cell marker.

Step S8: The main computer unit 20 proceeds to step S9 after assigning 3 points to the pertinent immune cell marker.

Step S9: The main computer unit 20 adds the points assigned to each of the individual immune cell markers and proceeds to step S17.

Step S10: Since the immune cell marker input through the input unit 10 is the CD4/CD8 T cell count ratio, the main computer unit 20 proceeds to step S11 if the immune cell marker input through the input unit 10 is less than 10%, or the main computer unit 20 proceeds to step S12 if the immune cell marker input through the input unit 10 is not less than 10%.

Step S11: The main computer unit 20 proceeds to step S9 after assigning 1 point to the pertinent immune cell marker.

Step S12: The main computer unit 20 judges whether the immune cell marker input through the input unit 10 is a cumulative frequency of 10% or more but less than 40%. If the result is affirmative, the main computer unit 20 proceeds to step S13, and if not, the main computer unit 20 proceeds to step S14.

Step S13: The main computer unit 20 proceeds to step S9 after assigning 2 points to the pertinent immune cell marker.

Step S14: The main computer unit 20 judges whether the immune cell marker input through the input unit 10 is a cumulative frequency of 40% or more but less than 80%. If the result is affirmative, the main computer unit 20 proceeds to step S15, and if not, the main computer unit 20 proceeds to step S16.

Step S15: The main computer unit 20 proceeds to step S9 after assigning 1 point to the pertinent immune cell marker.

Step S16: The main computer unit 20 proceeds to step S9 after assigning 2 points to the pertinent immune cell marker.

FIG. 10 is an explanatory diagram showing a specific example of points assigned to the individual immune cell markers that are added in step S9.

For example, if (a) T cell count=3, (b) T cell proliferation index=1, (c) CD4/CD8 T cell count ratio=2, (d) naive T cell count=3, (e) naive/memory T cell count ratio=2, (f) B cell count=3, (g) NK cell count=2, (h) IL-2 cytokine productivity=2, (i) IFN-γ cytokine productivity=3, and (j) IL-4 cytokine productivity=2 as depicted in this Figure, a score obtained by adding all these points is "23".

In steps S17 to S21 which follow hereunder, the main computer unit 20 judges to which one of the 5 grades of evaluation results the score belongs.

Step S17: The main computer unit 20 judges whether the score belongs grade 5. If the score is judged to belong to grade 5, the main computer unit 20 proceeds to step S21 with this result stored, and if not, the main computer unit 20 proceeds to step S18.

Step S18: The main computer unit 20 judges whether the score belongs to grade 4. If the score is judged to belong to grade 4, the main computer unit 20 proceeds to step S21 with this result stored, and if not, the main computer unit 20 proceeds to step S19.

Step S19: The main computer unit 20 judges whether the score belong to grade 3. If the score is judged to belong to grade 3, the main computer unit 20 proceeds to step S21 with this result stored, and if not, the main computer unit 20 proceeds to step S20.

In the case of the example shown in FIG. 10, the score is "23" so that the score is evaluated as belonging to grade 3.

Step S20: The main computer unit 20 judges whether the score belongs to grade 2. If the score is judged to belong to grade 2, the main computer unit 20 proceeds to step S21 with this result stored, and if not, the main computer unit 20 judges that the score belongs to grade 1 and proceeds to step S21 with this result stored.

Step S21: The main computer unit 20 displays a textual statement corresponding to the result of immunity grading on the display unit 40 and completes the evaluation process. The textual statement might be "The subject has sufficiently high immunity." for grade 5, "The subject has high immunity." for grade 4, "The subject has ordinary immunity or immunity in a stage of initial degradation." for grade 3, "The subject has slightly degraded immunity." for grade 2, and "The subject has highly degraded immunity." for grade 1, for example.

Since the score is evaluated as belonging to grade 3 in the case of the example shown in FIG. 10, the textual statement "The subject has ordinary immunity or immunity in a stage of initial degradation." would be displayed on the display unit 40.

These textual statements are stored in relation to grades 1 to 5 in the external storage device 30.

If necessary, the main computer unit 20 generates a radar graph or the like and displays the same on the display unit 40 or prints the same by executing a print job.

Additionally, the main computer unit 20 would presents comments on the immunity of each person on printing paper in consideration of the aforementioned radar graph, past illnesses, present illnesses and values of other persons whose blood has been sampled, for instance.

Figure 11:
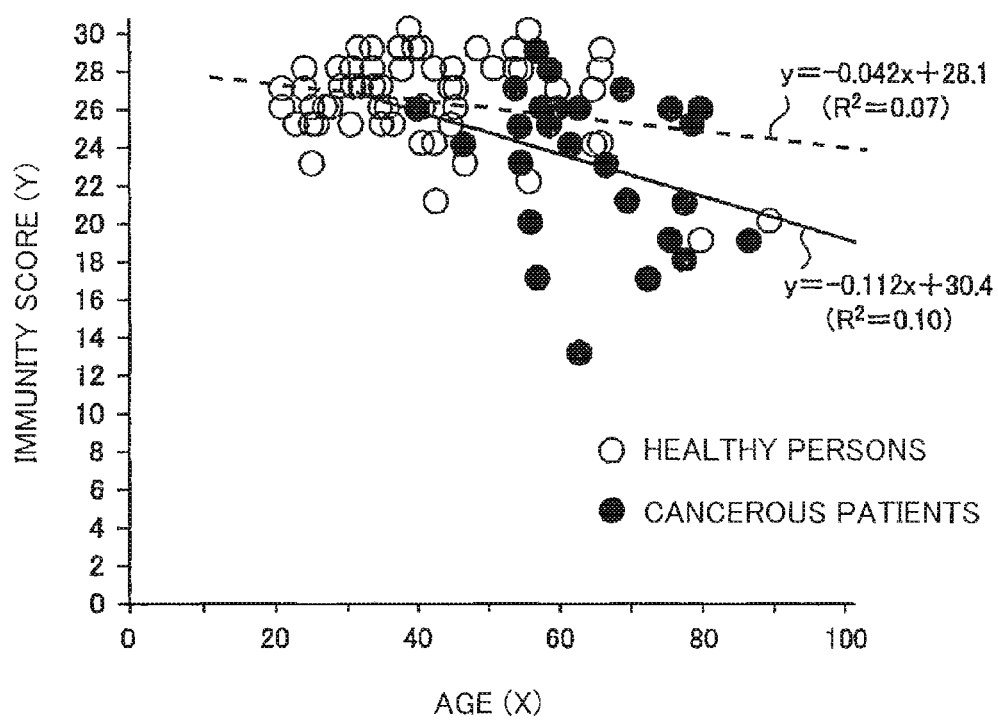
FIG. 11 is a correlation diagram showing a correlation between immunity score and age.

FIG. 11 is a correlation diagram showing a correlation between immunity score and age, in which the vertical axis y represents the immunity score and the horizontal axis x represents the age, R2 indicating regression coefficients.

As is apparent from this Figure, the ability of immune cells degrades as a result of aging. If populations and functions of 10 kinds of immune cells are measured and scored, it would be obvious that overall abilities of healthy persons of varying ages degrade with certainty due to aging.

Cancerous patients, on the other hand, show a different distribution from the healthy persons, that is, more cancerous patients obviously have lower scores than the healthy persons with respect to the overall abilities and, thus, the present invention is extremely useful in knowing human health conditions.

According to the present invention described thus far, general, comprehensive immunity of humans can be evaluated in an objective fashion. It is therefore possible to recognize one's own immunity in numerical form and find changes in the immunity by making measurements as appropriate, thereby making it possible to predict the occurrence of a disease from a reduction in evaluation results.

Also, as the general, comprehensive immunity can be objectively evaluated, it is possible to assess effects of various immunity recovery methods. For example, it is possible to assess the effect of dietary cure by making measurements before and after one month of the dietary cure.

Additionally, if a cancerous patient currently receives chemotherapy or the like, it is possible to monitor side effects on immunity. For example, while chemotherapy as applied to a cancerous patient exerts an effect of suppressing cancer in the bone marrow and the immune system, immunity degrades immediately after treatment and recovers after the treatment is stopped although the chemotherapeutic treatment is conducted at specific intervals.

If the immunity cannot recover as a result of repetitive treatment cycles, the patient will be placed at risk of infection. If the immunity is periodically evaluated with the present invention, it is possible to easily recognize a decrease in immunity and take measures to prevent infection.

It is to be pointed out that below-described variations of the foregoing embodiment are also embraced in the present invention.

While the embodiment has been described thus far with reference to an example in which progressively smaller numbers of points are assigned to individual levels of immunity as the immunity decreases, this arrangement may be so modified as to score the immunity by assigning progressively larger numbers of points as the immunity increases. In short, what is essential for the scoring scheme is that one should be allowed to distinguish between high and low levels of immunity.

Also, while the embodiment has been described thus far with reference to an example in which 1, 2 or 3 points are assigned to the three individual levels of immunity, this arrangement may be modified such that two levels or three or more levels of immunity are set depending on disease(s). The arrangement may also be modified such that a specific number of immunity levels are set according to age(s).

In addition, while the foregoing discussion has dealt with an example in which cytokines in the culture supernatant is analyzed by the ELISA analysis, the IL-2 cytokine productivity, the IFN-γ cytokine productivity and the IL-4 cytokine productivity may be determining by using real-time PCR analysis or a DNA array.

Furthermore, while the embodiment has been described thus far with reference to an example in which the external storage device with the database constructed therein is directly connected to the main computer unit, the present invention may be an immunity evaluation system which is configured such that one peripheral computer or at least two peripheral computers, each including an input unit and a display unit equivalent to those described earlier, and a database server storing immune cell markers serving as specific reference values for a plurality of immune cells in database form interconnected via electric communications lines, wherein each of the peripheral computers is provided with scoring means for scoring the immunity according to individual immune cell marker values for each of the preselected at least two immune cell markers based on the specific reference values and immunity evaluation means for evaluating the immunity based on a score obtained by adding up individual points given as a result of scoring. In this case, at least two peripheral computers (immunity evaluation apparatuses) can use the common database so that high efficiency is achieved.

Evaluation of Immunity Based on Immunity-Adjusted Age

While the embodiment has been described thus far with reference to the immunity evaluation method for evaluating a general immune function based on a score calculated by scoring the immunity from values of the immune cell markers and adding individual points obtained as a result of scoring, it is also possible to evaluate the general immune function from an immunity-adjusted age. An embodiment which uses the T cell proliferation index in evaluating the immunity based on the immunity-adjusted age is described hereunder.

First, the correlation between T cell proliferation index and age is determined from approximately 300 healthy persons. As previously discussed, the T cell proliferation index is obtained by measuring T cell proliferative activity of a healthy person against the anti-CD3 monoclonal antibody by the MTS method and calculating the T cell proliferation index by the following equation, where the absorbance is a value of the T cell proliferation index obtained by colorimetry:

(T cell proliferation index)=(absorbance OD)×(number of T cells in peripheral blood (cells/μl))/1000

Figure 12:
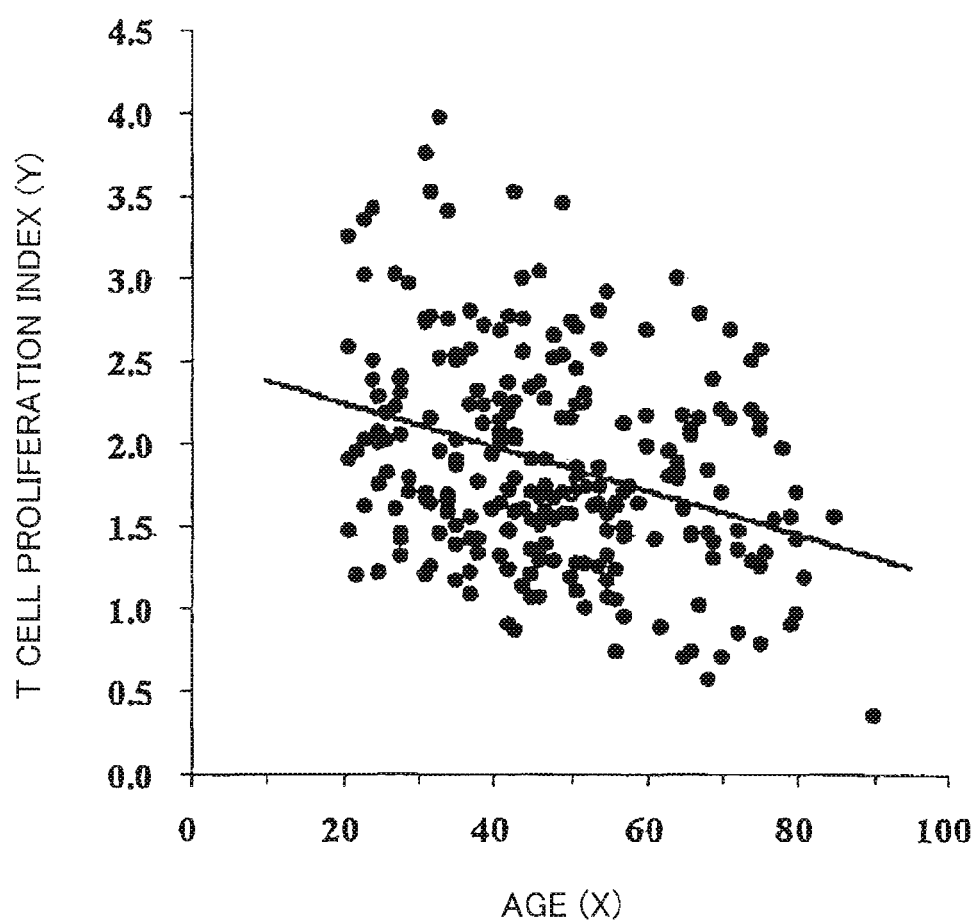
FIG. 12 is a correlation diagram showing a correlation between T cell proliferation index and age according to another embodiment of the present invention.

FIG. 12 is a diagram showing a correlation between the T cell proliferation index and age from approximately 300 healthy persons. The T cell proliferation index exhibits obvious changes during aging, thus showing a statistically significant correlation. Thus, from this correlation, a regression equation is calculated as follows:

y=−0.0174x+2.5348 where y indicates a value predicted for each age and x indicates true age.

Next, individual ages are entered into the regression equation thus obtained to thereby determine predicted values of the T cell proliferation index for the individual ages and calculate differences between the predicted values obtained and measured values of the T cell proliferation index as well as residual errors. Specifically, the residual errors are determined from residual error=(measured value (T cell proliferation index))−(predicted value (value obtained from the regression equation)).

Subsequently, immunity-adjusted ages are calculated. The immunity-adjusted age (calculated age) is determined by substituting the measured value of the T cell proliferation index of each subject into the following equation which is obtained by converting the aforementioned regression equation:

(Calculated age)=(2.5348−(measured value))/0.0174

The calculated age thus obtained is however an estimated value. Practically, it is more appropriate to express the immunity-adjusted age with a certain degree of allowance. As the residual errors which are the differences between the measured and predicted values of T cell proliferation indices assume a normal distribution, a range of the immunity-adjusted age is defined in the below-described manner.

Since the differences between the predicted and measured values of the T cell proliferation indices of the subjects, or the residual errors, follow a normal distribution, it is possible to obtain standard deviations of the residual errors from equations shown below.

$$\sigma'^2 = \frac{1}{n-1}\sum_{i=1}^{n}(x_i - \overline{x})^2$$

Figure 13:
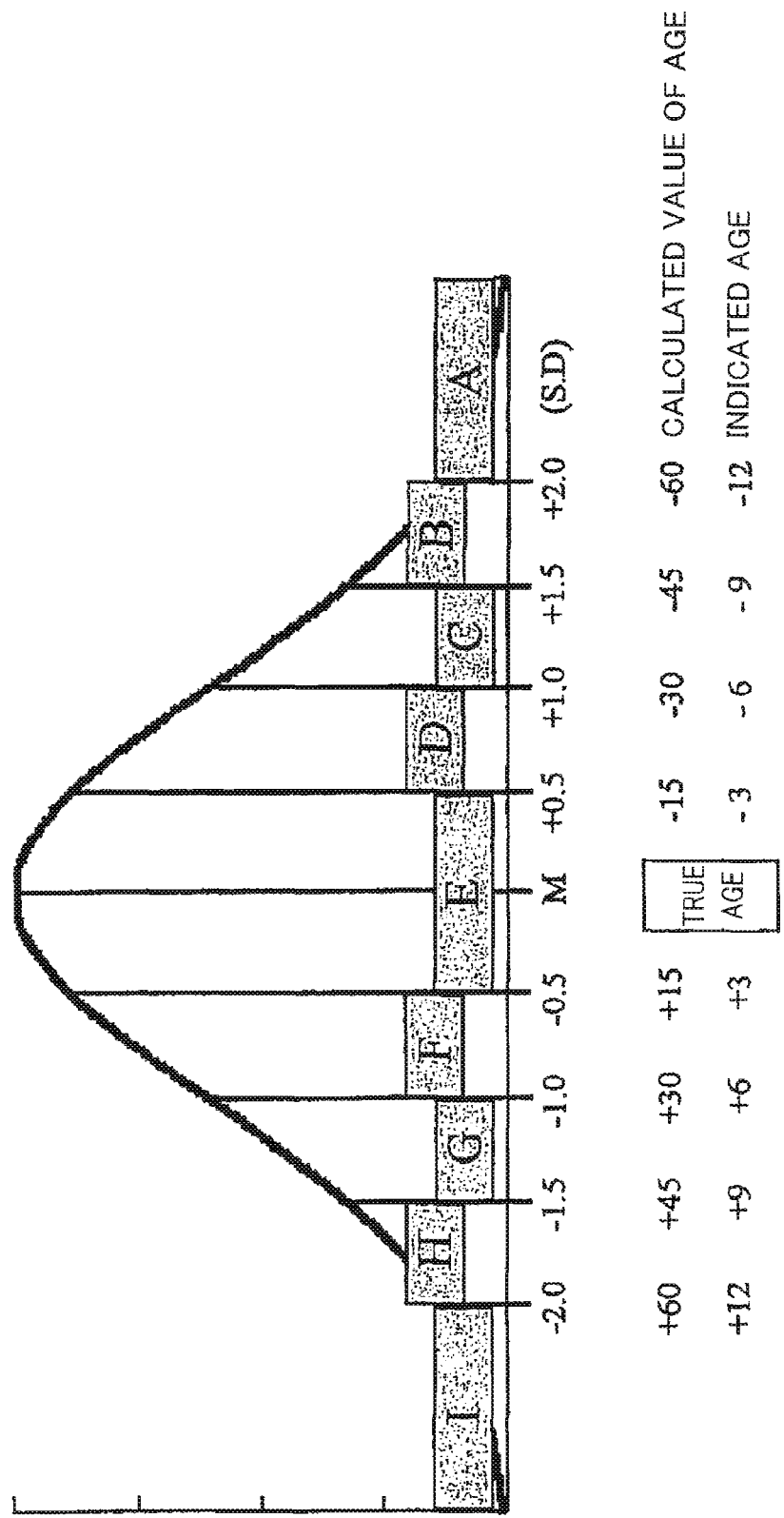
FIG. 13 is a diagram showing set ranges of age indication.

Ranges of age indication are set as shown in FIG. 13 based on the standard deviations SD of the residual errors obtained. Specifically, the ranges of age are ±0.5 SD, ±1.0 SD, ±1.5 SD and ±2.0 SD, wherein the residual errors are ±0.25 (0.5 SD), ±0.5 (1.0 SD), ±0.75 (1.5 SD) and ±1.0 (2.0 SD).

The inventors calculated differences between the true ages and immunity-adjusted ages of the subjects from the residual errors obtained based on these standard deviations. First, calculated ages are obtained from the aforementioned equation. Observation of differences between the calculated ages and the true ages reveals that values thereof obtained from the standard deviations coincide with each other for any ages. Particularly, ±0.5 SD indicates approximately ±15 years, ±1.0 SD indicates approximately ±30 years, ±1.5 SD indicates approximately ±45 years, ±2.0 SD indicates approximately ±60 years, and ±2.0 SD or above indicates approximately ±60 years for individual ages.

In actual calculation, a calculated age when shifted in a +1 SD direction is obtained by determining a predicted value of the T cell proliferation index by first substituting a true age into the regression equation and, then, substituting a value obtained by adding a residual error corresponding to the predicted value into the equation for calculating the calculated age.

(A) For age 40, the predicted value +1 SD is calculated as age 11.253 by 1.839+0.5=2.339;
(B) For age 50, the predicted value +1 SD is calculated as age 21.253 by 1.665+0.5=2.165; and
(C) For age 60, the predicted value +1 SD is calculated as age 31.253 by 1.491+0.5=1.991.

It follows that the difference between the calculated age and the true age is approximately 30 years regardless of age. The ranges of age with individual SD ranges mentioned above have been calculated in the above-described manner. The immunity-adjusted age is set within a range of approximately age 17-99 so that the immunity-adjusted age corresponds to the value of substantial age. Thus, the difference between the calculated age and the true age obtained as discussed above is assumed to be 20% and referred to as an "indicated age" so that the immunity-adjusted ages fall within this range. Specifically, the indicated age is calculated by the following equation:

(Indicated age)=(true age)+((calculated age)−(true age))×0.2

Next, the structure of an immunity evaluation apparatus practically used for performing immunity evaluation of the present embodiment is described. The overall structure of the immunity evaluation apparatus of this embodiment is the same as shown in FIG. 1.

It is to be noted, however, the input unit 10 includes a keyboard and a mouse, for example, through which information related to persons subjected to immunity evaluation (i.e., persons whose blood has been sampled), immune cell marker values including in particular T cell proliferation indices, and information related to healthy persons including in particular true ages thereof, and so on, can be input.

The database 50 of the external storage device 30 is for storing data on immune cell marker values of a healthy person used as specific reference values for a plurality of immune cells and information related to the healthy person in an interrelated manner. The database 50 is so configured that immune cell marker values of a new healthy person can be additionally stored when appropriate through the aforementioned input unit 10. The evaluation table 80 of the external storage device 30 stores, besides the evaluation table described in the foregoing embodiment obtained by classifying immunity evaluation results in a stepwise form according to gained points, an evaluation table (FIG. 16) representing later-described immunity evaluation classification of measured values and predicted values of T cell proliferation indices and immunity-adjusted ages.

Figure 14:
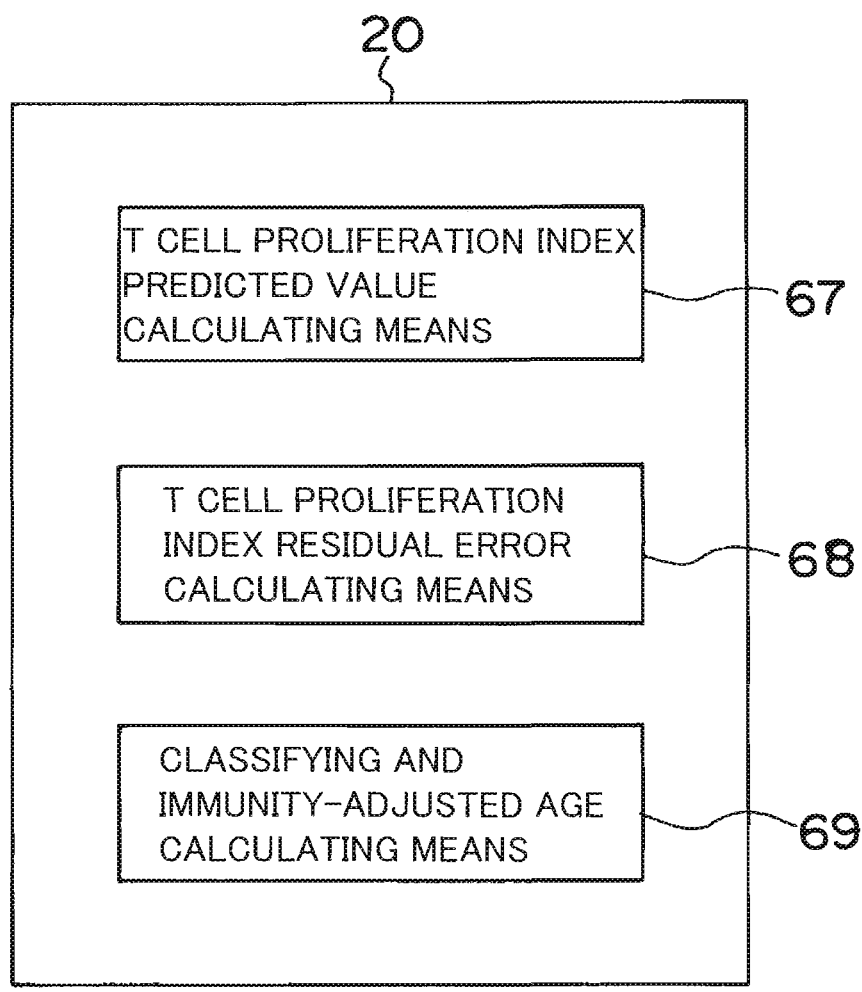
FIG. 14 is a block diagram showing functions possessed by a main computer unit according to the "another" embodiment.
Figure 18:
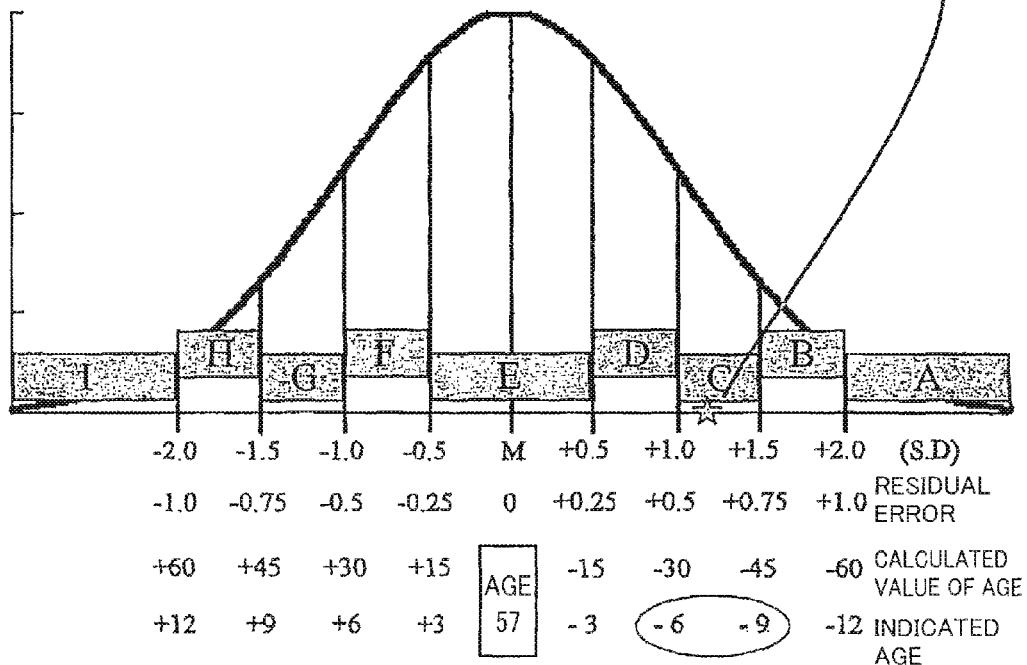
FIG. 18 is a diagram showing immunity evaluation classification and an immunity-adjusted age determined for another particular sample.
Figure 19:
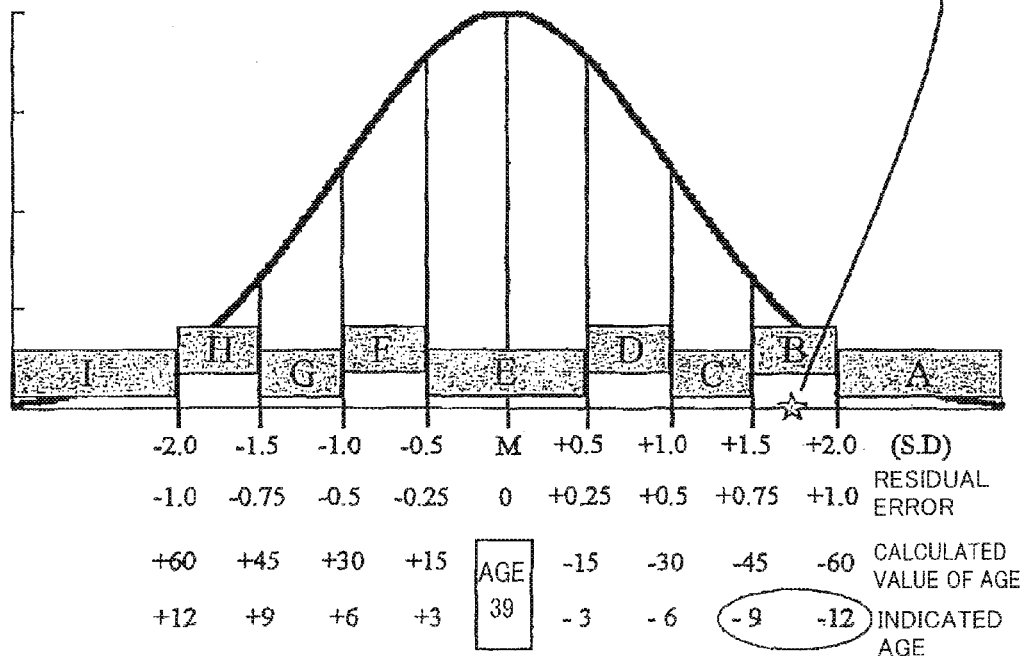
FIG. 19 is a diagram showing immunity evaluation classification and an immunity-adjusted age determined for another particular sample.
Figure 21:
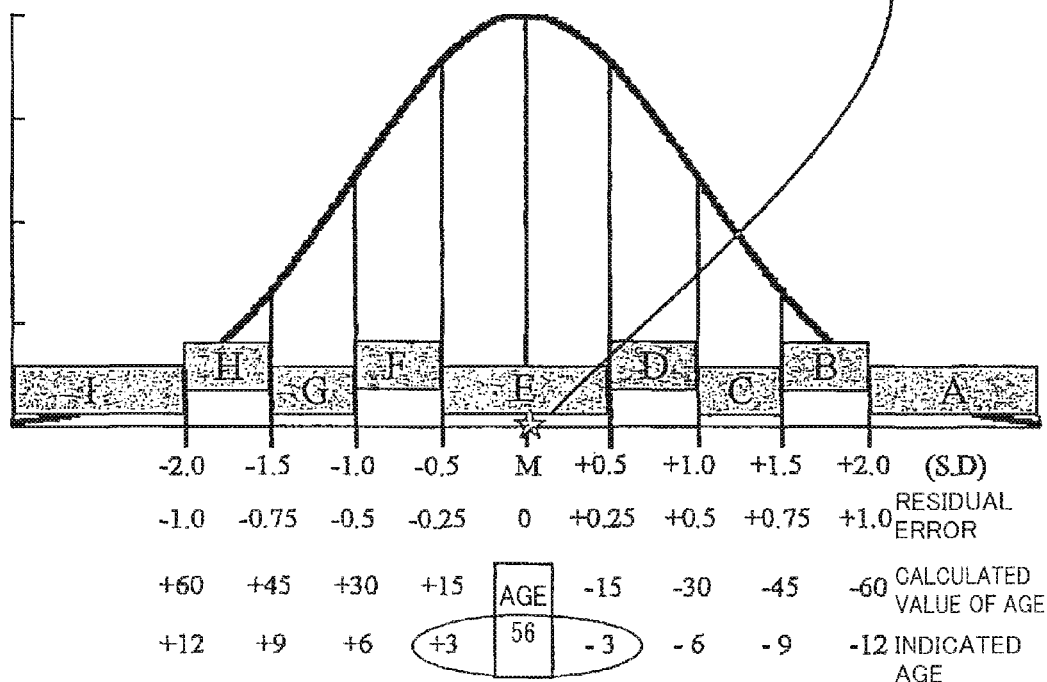
FIG. 21 is a diagram showing immunity evaluation classification and an immunity-adjusted age determined for another particular sample.

The immunity evaluation program is a program programmed by using a known programming language that causes the main computer unit to operate based on an immunity evaluation method according to the present embodiment described hereinbelow. This program, when executed, provides the main computer unit 20 with a function of T cell proliferation index predicted value calculating means 67, a function of T cell proliferation index residual error calculating means 68 and a function of classifying and immunity-adjusted age calculating means 69 for immunity classifying and immunity-adjusted age calculation based on the T cell proliferation indices, in addition to or separately from the function of the scoring means 60, the function of the adding means 61, the function of the immunity evaluation means 62, the function of the marker selection means 63, the function of the evaluation level setting means 64, the function of the score level setting means 65 and the function of the marker extraction means 66 as shown in FIG. 14.

While this immunity evaluation program is stored in the external storage device 30, the invention is not limited to this structure but the immunity evaluation program may be recorded in any of various information storage media, such as a portable magnetic disk, a magneto-optic disk and a semiconductor memory. This means that an arrangement may be made such that the immunity evaluation program can be installed when the need arises. If the immunity evaluation program is recorded in a portable data recording medium, the immunity evaluation program can easily be upgraded to an improved version.

The immunity evaluation program may be recorded in the data recording medium not only in a readily executable form but in a compressed or encrypted form.

The main computer unit 20, and thus the immunity evaluation apparatus A, exhibits the following functions by executing the aforementioned immunity evaluation program.

(1) A function to calculate a predicted value of a T cell proliferation index by substituting an input true age into the regression equation which has been predetermined and recorded (T cell proliferation index predicted value calculating means 67).

(2) A function to calculate a residual error of the T cell proliferation index from an input measured value of the T cell proliferation index and a predicted value thereof obtained in step S32 (T cell proliferation index residual error calculating means 68).

(3) A function to classify the immunity and calculate an immunity-adjusted age based on the residual error obtained (classifying and immunity-adjusted age calculating means 69).

FIG. 15 is a flowchart for explaining an example of an immunity evaluation process performed by the main computer unit 20 based on a measured value of the T cell proliferation index and true age input through the input unit 10.

Step S31: The information related to persons subjected to immunity evaluation, such as the address, name, age, sex, past illnesses, present illnesses, and so on, of each person, as well as immune cell marker values including T cell proliferation indices are input through the input unit 10. The main computer unit 20 proceeds to step S32 when the enter key is pressed.

Step S32: The main computer unit 20 calculates a predicted value of a T cell proliferation index by substituting an input true age into the regression equation which has been predetermined and recorded.

Step S33: The main computer unit 20 calculates a residual error of the T cell proliferation index from an input measured value of the T cell proliferation index and a predicted value thereof obtained in step S32.

Step S34: The main computer unit 20 judges in which one of ranks "A" to "I" shown in FIG. 16 the measured value is to be assigned based on the residual error obtained, that is, based on the predicted value and the measured value, and then determines the immunity-adjusted age. Specifically, the evaluation table 80 stores the evaluation table representing immunity evaluation classification of measured values and predicted values of T cell proliferation indices and immunity-adjusted ages as shown in FIG. 16. In step S34, the main computer unit 20 ranks the immunity based on the measured value and the predicted value and calculates the immunity-adjusted age using this evaluation table. Among the immunity-adjusted ages shown in FIG. 16, a youngest age range is set as ages 17-20 and an oldest age range is set as ages 96-99.

Step S35: The main computer unit 20 displays evaluation results obtained by the foregoing steps on the display unit 40 and completes the evaluation process. Included in contents of evaluation are the "information related to the persons subjected to immunity evaluation including true ages thereof", "measured values of the T cell proliferation indices", "predicted values of the T cell proliferation indices", "residual errors", "immunity evaluation ranks", "immunity-adjusted ages", and so forth.

FIGS. 17-21 show immunity evaluation ranks and immunity-adjusted ages actually determined for 5 samples.

For example, while the sample (case 1) of FIG. 17 has a true age of 68, the measured value of the T cell proliferation index is 0.58 and the residual error is −0.77. Accordingly, this sample is classified in immunity evaluation rank H and evaluated as having an immunity-adjusted age of 77-80 which is older than the true age. Also, while the sample (case 2) of FIG. 18 has a true age of 57, the measured value of the T cell proliferation index is 2.11 and the residual error is 0.57. Accordingly, this sample is classified in immunity evaluation rank C and evaluated as having an immunity-adjusted age of 48-51 which is younger than the true age. While the sample (case 3) of FIG. 19 has a true age of 39, the measured value of the T cell proliferation index is 2.72 and the residual error is 0.86. Accordingly, this sample is classified in immunity evaluation rank B and evaluated as having an immunity-adjusted age of 27-30 which is much younger than the true age. While the sample (case 4) of FIG. 20 has a true age of 72, the measured value of the T cell proliferation index is 0.85 and the residual error is −0.43. Accordingly, this sample is classified in immunity evaluation rank F and evaluated as having an immunity-adjusted age of 75-78 which is older than the true age. While the sample (case 5) of FIG. 18 has a true age of 56, the measured value of the T cell proliferation index is 1.63 and the residual error is 0.07. Accordingly, this sample is classified in immunity evaluation rank E and evaluated as having an immunity-adjusted age of 53-59 which is in agreement with the true age.

As discussed so far, the immunity is expressed in terms of age by using the T cell proliferation index which is highly correlated with age in the present embodiment, so that it is possible to objectively evaluate the general, comprehensive immunity.

While the present embodiment is intended to evaluate the general immune function according to the immunity-adjusted age determined based on the measured value of the T cell proliferation index, it goes without saying that the immunity evaluation apparatus of this embodiment may be so configured as to further possess the functions of the foregoing embodiment to score the immunity according to individual immune cell marker values and evaluate the general immune function based on a score obtained by adding individual points acquired as a result of scoring.

Described next is an embodiment which utilizes reexpression of CD3 in evaluating the immunity based on the immunity-adjusted age.

First, a correlation between the quantity of expressed CD3 and age is determined from approximately 300 healthy persons. A method of determining the quantity of expressed CD3 is as follows. T cells enter a multiplicative growth phase when stimulated by the anti-CD3 monoclonal antibody. At the same time, CD3 antigen present on a cell membrane surface combines with the anti-CD3 monoclonal antibody and is taken into the cells, and is thus no longer present on cell surface. It takes two to three days for the quantity of CD3 on the cell membrane to return to an original level. The inventors stimulated the T cells in healthy persons by the anti-CD3 monoclonal antibody and measured CD3 in the T cells after three days.

Figure 22:
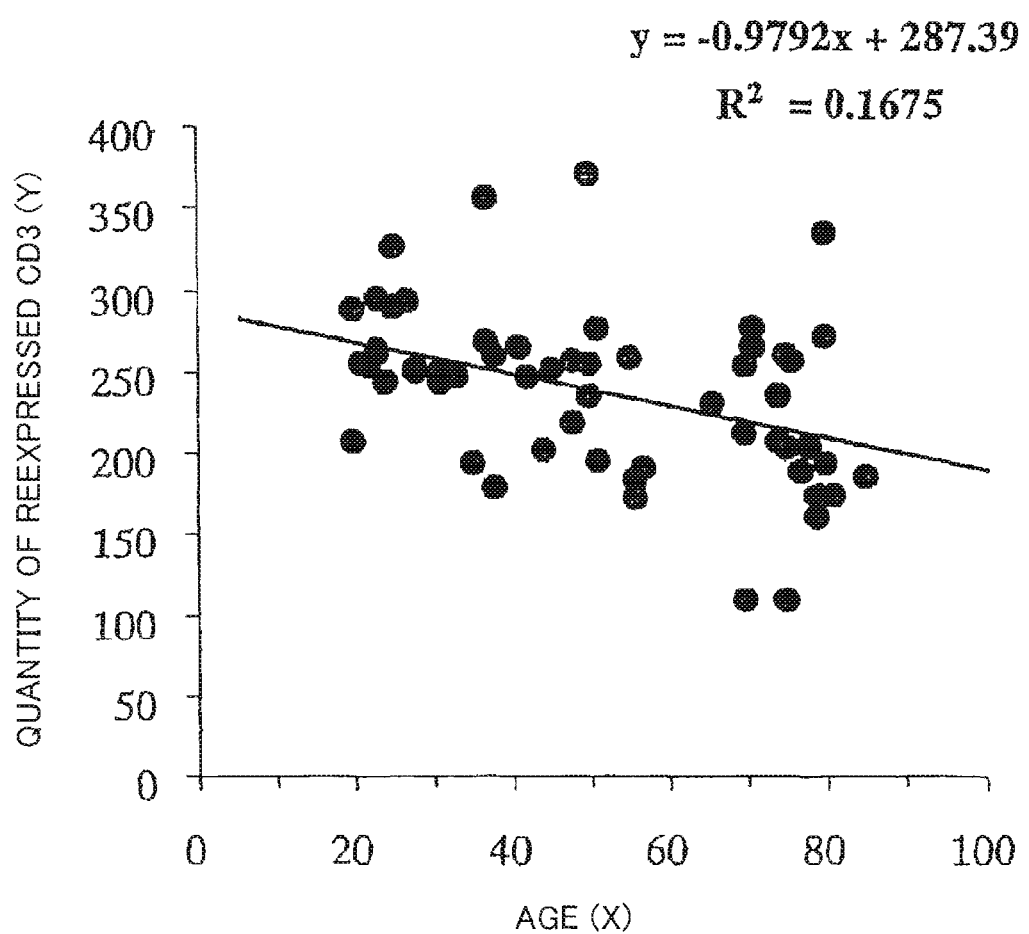
FIG. 22 is a correlation diagram showing a correlation between the quantity of expressed CD3 and age according to still another embodiment of the present invention.

FIG. 22 is a correlation diagram showing a correlation between the quantity of reexpressed CD3 and age from approximately 300 healthy persons. The quantity of CD3 exhibits obvious changes during aging, thus showing a statistically significant correlation. Thus, from this correlation, a regression equation is calculated as follows, indicating that the quantity of CD3 reduces with increasing age:

$$y=0.9782x+287.39$$

where y indicates a value predicted for each age and x indicates true age.

Next, individual ages are entered into the regression equation thus obtained to thereby determine predicted values of the quantities of reexpressed CD3 for the individual ages and calculate differences between the predicted values obtained and measured values of the T cell proliferation index as well as residual errors. Specifically, the residual errors are determined from residual error=(measured value (quantity of reexpressed CD3))−(predicted value (value obtained from the regression equation)).

Subsequently, immunity-adjusted ages are calculated. The immunity-adjusted age (calculated age) is determined by substituting the measured value of the quantity of reexpressed CD3 of each subject into the following equation which is obtained by converting the aforementioned regression equation:

$$(\text{Calculated age})=(287.39-(\text{measured value}))/0.9782$$

The calculated age thus obtained is however an estimated value. Practically, it is more appropriate to express the immunity-adjusted age with a certain degree of allowance. As is the case with the T cell proliferation index, a range of the immunity-adjusted age is defined by utilizing the fact that the residual errors which are the differences between the measured and predicted values of the quantities of reexpressed CD3 assume a normal distribution.

The immunity-adjusted age is set within a range of approximately age 17-99 so that the immunity-adjusted age corresponds to the value of substantial age. Thus, the difference between the calculated age and the true age obtained as discussed above is assumed to be 20% and referred to as an "indicated age" so that the immunity-adjusted ages fall within this range. Specifically, the indicated age is calculated by the following equation:

$$(\text{Indicated age})=(\text{true age})+((\text{calculated age})-(\text{true age}))\times 0.2$$

The structure of an immunity evaluation apparatus, the configuration of a program, the configuration of an evaluation table, and functions thereof practically used for performing immunity evaluation of the present embodiment are exactly the same as those used in the case of the T cell proliferation index.

It is to be noted, however, the input unit 10 includes a keyboard and a mouse, for example, through which information related to persons subjected to immunity evaluation (i.e., persons whose blood has been sampled), immune cell marker values including in particular the quantities of reexpressed CD3, and information related to healthy persons including in particular true ages thereof, and so on, can be input.

The database 50 of the external storage device 30 is for storing data on immune cell marker values of a healthy person used as specific reference values for a plurality of immune cells and information related to the healthy person in an interrelated manner. The database 50 is so configured that immune cell marker values of a new healthy person can be additionally stored when appropriate through the aforementioned input unit 10. The evaluation table 80 of the external storage device 30 stores, besides the evaluation table described in the foregoing embodiment obtained by classifying immunity evaluation results in a stepwise form according to gained points, an evaluation table (same as shown in FIG. 16) representing later-described immunity evaluation classification of measured values and predicted values of the quantities of reexpressed CD3 and immunity-adjusted ages.

Figure 23:
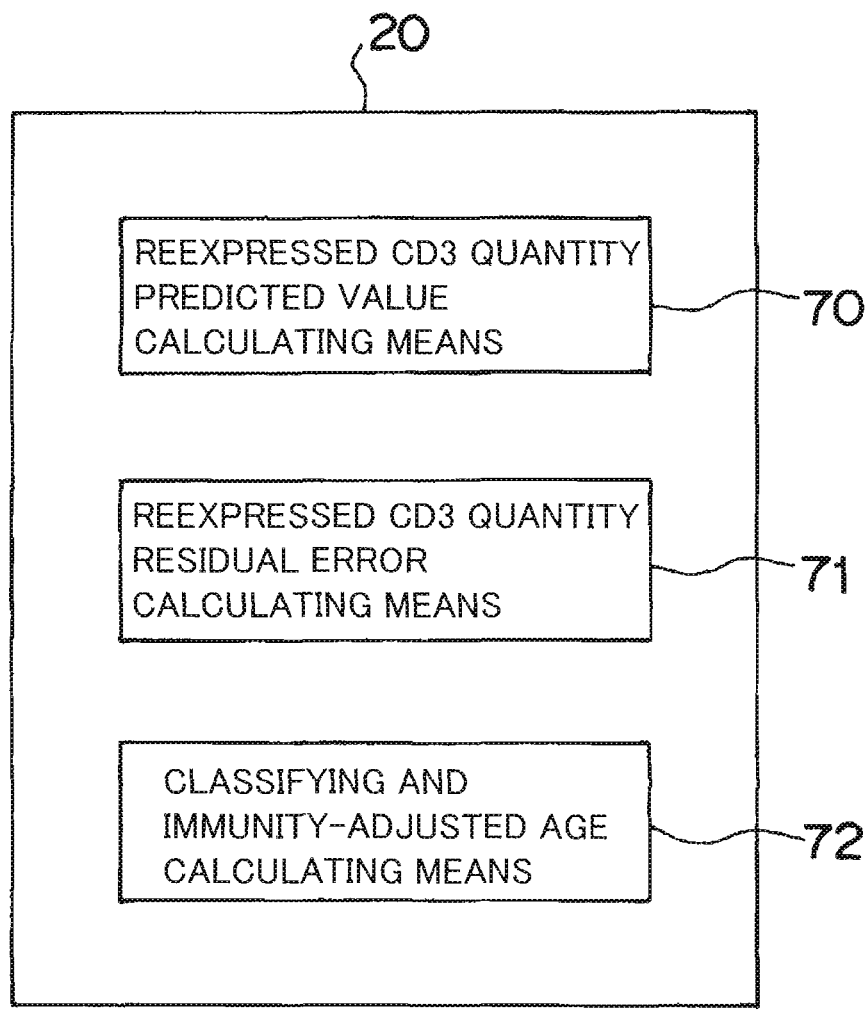
FIG. 23 is a block diagram showing functions possessed by a main computer unit according to the "still another" embodiment.

The immunity evaluation program is a program programmed by using a known programming language that causes the main computer unit to operate based on an immunity evaluation method according to the present embodiment described hereinbelow. This program, when executed, provides the main computer unit 20 with a function of reexpressed CD3 quantity predicted value calculating means 70, a function of reexpressed CD3 quantity residual error calculating means 71 and a function of classifying and immunity-adjusted age calculating means 72 for immunity classifying and immunity-adjusted age calculation based on the quantities of reexpressed CD3, in addition to or separately from the function of the scoring means 60, the function of the adding means 61, the function of the immunity evaluation means 62, the function of the marker selection means 63, the function of the evaluation level setting means 64, the function of the score level setting means 65 and the function of the marker extraction means 66 as shown in FIG. 23.

While this immunity evaluation program is stored in the external storage device 30, the invention is not limited to this structure but the immunity evaluation program may be recorded in any of various information storage media, such as a portable magnetic disk, a magneto-optic disk and a semiconductor memory. This means that an arrangement may be made such that the immunity evaluation program can be installed when the need arises. If the immunity evaluation program is recorded in a portable data recording medium, the immunity evaluation program can easily be upgraded to an improved version.

The immunity evaluation program may be recorded in the data recording medium not only in a readily executable form but in a compressed or encrypted form.

The main computer unit 20, and thus the immunity evaluation apparatus A, exhibits the following functions by executing the aforementioned immunity evaluation program.

(1) A function to calculate a predicted value of the quantity of reexpressed CD3 by substituting an input true age into the regression equation which has been predetermined and recorded (reexpressed CD3 quantity predicted value calculating means 70).

(2) A function to calculate a residual error of the quantity of reexpressed CD3 from an input measured value of the quantity of reexpressed CD3 and a predicted value thereof obtained in step S32 (reexpressed CD3 quantity residual error calculating means 71).

(3) A function to classify the immunity and calculate an immunity-adjusted age based on the residual error obtained (classifying and immunity-adjusted age calculating means 72).

Figure 24:
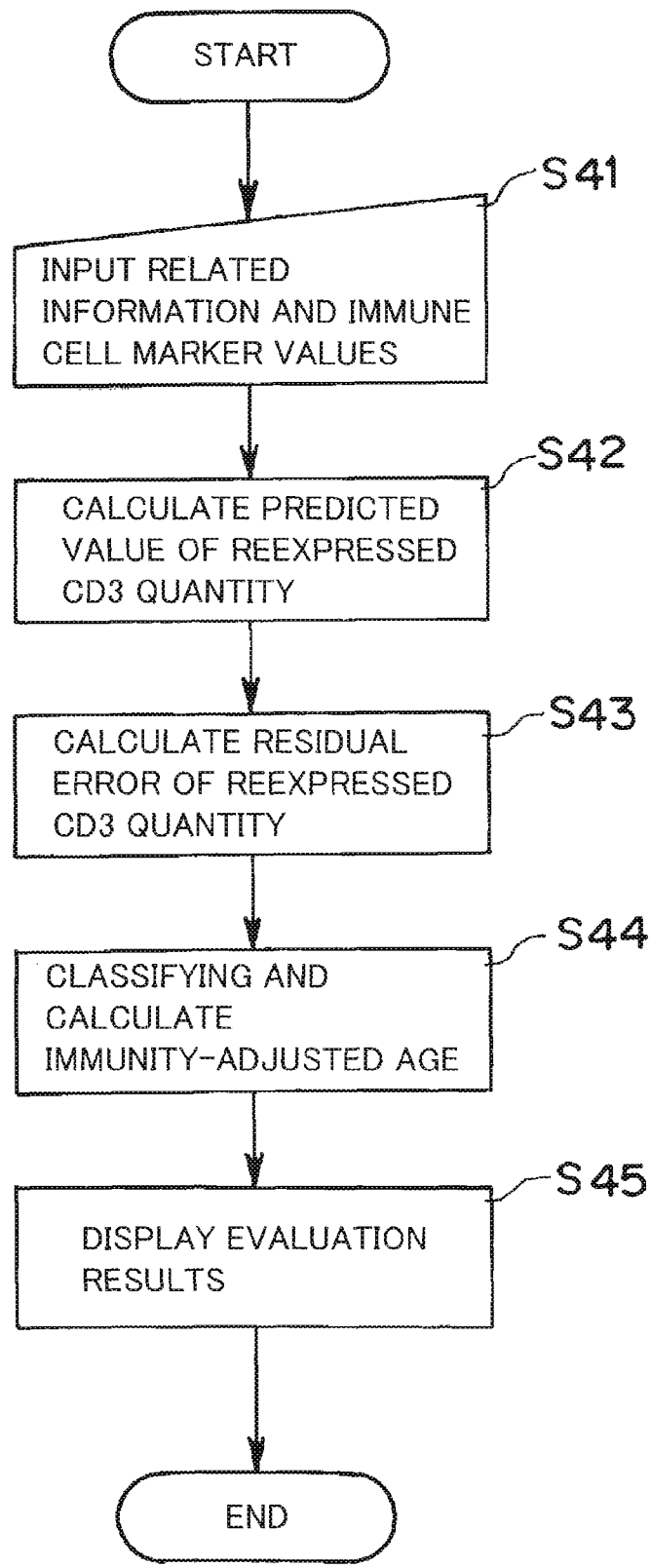
FIG. 24 is a flowchart for explaining an example of an immunity evaluation process performed by the main computer unit.

FIG. 24 is a flowchart for explaining an example of an immunity evaluation process performed by the main computer unit 20 based on a measured value of the quantity of reexpressed CD3 and true age input through the input unit 10.

Step S41: The information related to persons subjected to immunity evaluation, such as the address, name, age, sex, past illnesses, present illnesses, and so on, of each person, as well as immune cell marker values including the quantity of reexpressed CD3 are input through the input unit 10. The main computer unit 20 proceeds to step S32 when the enter key is pressed.

Step S42: The main computer unit 20 calculates a predicted value of the quantity of reexpressed CD3 by substituting an input true age into the regression equation which has been predetermined and recorded.

Step S43: The main computer unit 20 calculates a residual error of the quantity of reexpressed CD3 from an input measured value of the quantity of reexpressed CD3 and a predicted value thereof obtained in step S32.

Step S44: The main computer unit 20 judges in which one of ranks "A" to "I" shown in FIG. 16 the measured value is to be assigned based on the residual error obtained, that is, based on the predicted value and the measured value, and then determines the immunity-adjusted age. Specifically, the evaluation table 80 stores the evaluation table representing immunity evaluation classification of measured values and predicted values of the quantity of reexpressed CD3 and immunity-adjusted ages as shown in FIG. 16. In step S44, the main computer unit 20 classifies the immunity based on the measured value and the predicted value and calculates the immunity-adjusted age using this evaluation table. Among the immunity-adjusted ages shown in FIG. 16, the youngest age range is set as ages 17-20 and the oldest age range is set as ages 96-99.

Step S45: The main computer unit 20 displays evaluation results obtained by the foregoing steps on the display unit 40 and completes the evaluation process. Included in contents of evaluation are the "information related to the persons subjected to immunity evaluation including true ages thereof", "measured values of the quantity of reexpressed CD3", "predicted values of the quantity of reexpressed CD3", "residual errors", "immunity evaluation ranks", "immunity-adjusted ages", and so forth.

As discussed so far, the immunity is expressed in terms of age by using the quantity of reexpressed CD3 which is highly correlated with age in the present embodiment, so that it is possible to objectively evaluate the general, comprehensive immunity.

While the present embodiment is intended to evaluate the general immune function according to the immunity-adjusted age determined based on the measured value of the quantity of reexpressed CD3, it goes without saying that the immunity evaluation apparatus of this embodiment may be so configured as to further possess the functions of the foregoing embodiment to score the immunity according to individual immune cell marker values and evaluate the general immune function based on a score obtained by adding individual points acquired as a result of scoring.

All of the foregoing embodiments are simply illustrative and not limiting the present invention. Various modifications and alterations of the embodiments are possible in implementing this invention. Accordingly, the scope of the invention is defined solely by the appended claims and equivalents thereof.

The invention claimed is:

1. A method for evaluating the immunity status of a subject based on immune cells parameters in a blood sample from the subject, the method comprising the steps of:

(i) obtaining a blood sample from a subject and determining the values of at least two immune cell parameters in the blood sample, wherein said immune cell parameters include T cell count and T cell proliferation index, said T cell proliferation index being the product of T cell counts and T cell proliferation activity, wherein T cell proliferation activity is determined by collecting mononuclear cells by culturing them in the presence of a mitogenic agent, and determining the number of live cells in the sample of stimulated mononuclear cells using an assay, wherein T cell proliferation activity is measured;

(ii) providing a database stored in a storage unit, the database comprising the values of said immune cell parameters of a plurality of healthy subjects, wherein the values of said immune cell parameters are ranked in a stepwise manner from low values to high values based on the cumulative frequency of said immune cell parameters in a plurality of healthy subjects, each step being accorded a specific numerical score;

(iii) assigning a numerical score to each of the immune cell parameters of the subject by executing a scoring operation, wherein the value of each immune cell parameter determined in step (i) is compared to the values of the same immune cell parameters stored in the database provided in step (ii), the numerical score assigned to each immune cell parameter being related to the numerical score of the corresponding value of same parameter stored in the database;

(iv) calculating the immunity score of the subject as the sum of the numerical scores assigned to each of the immune parameters in step (iii);

(v) providing a database stored in a storage unit, the database comprising immunity scores of a plurality of healthy subjects, wherein the immunity scores are ranked in a stepwise manner from low immunity scores to high immunity scores based on the cumulative frequency of immunity scores in a plurality of healthy subjects, wherein ranges of immunity scores are identified as at least two level immunities from low immunity to high immunity, and (vi) comparing the immunity score of the subject calculated in step (iv) to immunity scores stored in the database provided in step (v) to thereby evaluate the immunity status of the subject as one of low immunity, normal immunity and high immunity.

2. The method according to claim 1, wherein the at least two immune cell parameters further include at least one of a CD4/CD8 T cell count ratio, a naive T cell count, a naive/memory T cell count ratio, IL-2 cytokine productivity, IFN-gamma cytokine productivity, IL-4 cytokine productivity, a B cell count or an NK cell count.

* * * * *